US008697772B2

(12) United States Patent
Blömker et al.

(10) Patent No.: US 8,697,772 B2
(45) Date of Patent: Apr. 15, 2014

(54) POLYMERIZABLE PHOSPHORIC ACID DERIVATIVES COMPRISING A POLYALICYLIC STRUCTURE ELEMENT

(75) Inventors: Tobias Blömker, Cuxhaven (DE); Manfred Stepputtis, Kutenholz (DE); Manfred Thomas Plaumann, Cuxhaven (DE)

(73) Assignee: VOCO GmbH, Cuxhaven (DE)

( * ) Notice: Subject to any disclaimer, the term of this patent is extended or adjusted under 35 U.S.C. 154(b) by 182 days.

(21) Appl. No.: 13/291,645

(22) Filed: Nov. 8, 2011

(65) Prior Publication Data

US 2012/0115108 A1 May 10, 2012

(30) Foreign Application Priority Data

Nov. 8, 2010 (DE) .......................... 10 2010 043 571
Nov. 7, 2011 (EP) ..................................... 11188086

(51) Int. Cl.
*A61K 6/08* (2006.01)
(52) U.S. Cl.
USPC ............... 523/116; 523/105; 523/1; 528/242; 528/480

(58) Field of Classification Search
USPC ................. 523/116, 105, 1; 528/242, 480
See application file for complete search history.

(56) References Cited

U.S. PATENT DOCUMENTS

| | | | |
|---|---|---|---|
| 1,019,293 A | 3/1912 | Samuel | |
| 3,200,142 A | 8/1965 | Bowen | |
| 4,148,988 A | 4/1979 | Masuhara et al. | |
| 4,447,520 A | 5/1984 | Henne et al. | |
| 4,514,342 A * | 4/1985 | Billington et al. | 558/180 |
| 4,772,530 A | 9/1988 | Gottschalk et al. | |
| 4,830,616 A | 5/1989 | Okuda et al. | |
| 4,868,091 A | 9/1989 | Boettcher et al. | |
| 4,874,450 A | 10/1989 | Gottschalk | |
| 4,954,414 A | 9/1990 | Adair et al. | |
| 5,055,372 A | 10/1991 | Shanklin et al. | |
| 5,057,393 A | 10/1991 | Shanklin et al. | |
| 5,761,169 A | 6/1998 | Mine | |
| 6,670,499 B1 * | 12/2003 | Inoue et al. | 560/117 |
| 6,794,528 B2 | 9/2004 | Onchi | |
| 7,081,485 B2 | 7/2006 | Suh | |
| 7,148,382 B2 | 12/2006 | Wolf | |
| 2006/0246017 A1 * | 11/2006 | Klee et al. | 424/57 |
| 2007/0027229 A1 | 2/2007 | Moszner et al. | |

FOREIGN PATENT DOCUMENTS

| | | |
|---|---|---|
| DD | 10119831 A1 | 10/2002 |
| DE | 3236026 A1 | 3/1984 |
| DE | 3338077 A1 | 5/1985 |
| DE | 3703120 A1 | 1/1988 |
| DE | 4416857 C1 | 6/1995 |
| DE | 19903177 | 7/2000 |
| DE | 19961347 A1 | 6/2001 |
| DE | 4231579 C2 | 11/2002 |
| DE | 10352260 B3 | 4/2005 |
| DE | 60116142 T2 | 1/2006 |
| DE | 102004060285 A1 | 6/2006 |
| DE | 102006019092 A1 | 3/2007 |
| DE | 60312714 T2 | 12/2007 |
| DE | 102006050153 A1 | 5/2008 |
| EM | 0321683 A1 | 6/1989 |
| EP | 0007508 A2 | 2/1980 |
| EP | 0059451 A1 | 2/1982 |
| EP | 0047902 A2 | 3/1982 |
| EP | 0049631 A1 | 4/1982 |
| EP | 0057474 A2 | 8/1982 |
| EP | 0074708 A2 | 3/1983 |
| EP | 0141324 A2 | 5/1985 |
| EP | 0173567 A2 | 5/1986 |
| EP | 0184095 A2 | 6/1986 |
| EP | 0206074 A2 | 12/1986 |
| EP | 0209700 A2 | 1/1987 |
| EP | 0325266 A2 | 7/1989 |
| EP | 0366977 A2 | 5/1990 |
| EP | 0546648 A1 | 6/1993 |
| EP | 0611752 A1 | 8/1994 |
| EP | 0684033 A1 | 11/1995 |
| EP | 0684034 A1 | 11/1995 |
| EP | 0783880 A2 | 7/1997 |
| EP | 0909761 A1 | 4/1999 |
| EP | 0948955 A1 | 10/1999 |
| EP | 0980682 A1 | 2/2000 |
| EP | 1148060 A1 | 9/2003 |
| EP | 1346717 A1 | 9/2003 |
| EP | 1084131 A1 | 11/2003 |
| EP | 1148071 A2 | 6/2004 |
| EP | 1454911 A1 | 9/2004 |
| EP | 1563821 A1 | 8/2005 |
| EP | 1236459 B1 | 11/2005 |
| EP | 1238993 A1 | 11/2005 |
| EP | 1721949 A1 | 11/2006 |
| EP | 1112995 B1 | 4/2007 |
| EP | 1839640 A2 | 10/2007 |
| FO | 8916628 A1 | 6/1990 |
| GB | 1110673 A | 4/1968 |
| GB | 2000789 B1 | 1/1979 |
| GB | 2093458 A | 9/1982 |
| GB | 2310855 | 10/1997 |
| JP | 7-206740 | 8/1995 |
| JP | 2007091642 A * | 4/2007 |
| WO | 00059451 A1 | 10/2000 |
| WO | 02092021 A1 | 11/2002 |
| WO | 02092023 A1 | 11/2002 |
| WO | 2005084611 A1 | 9/2005 |
| WO | 2006063891 A1 | 6/2006 |
| WO | 2006111373 A1 | 10/2006 |
| WO | 2009065873 A2 | 5/2009 |

* cited by examiner

*Primary Examiner* — James J Seidleck
*Assistant Examiner* — Peter A Salamon
(74) *Attorney, Agent, or Firm* — Duane Morris LLP; J. Rodman Steele, Jr.; Gregory M. Lefkowitz

(57) ABSTRACT

Certain novel polymerizable phosphoric acid derivatives (hereinafter referred to as monomers) comprising a polyalicyclic structure element, mixtures comprising one or a plurality of these compounds and corresponding curable blends and products as well as their respective use as a dental material or for the preparation of a dental material are described. The compounds are eminently suitable as bonding agents, in particular in dental adhesive materials. A process for preparing these compounds or mixtures and a method for preparing a product, preferably a product suitable for dentistry, are also described.

21 Claims, No Drawings

POLYMERIZABLE PHOSPHORIC ACID DERIVATIVES COMPRISING A POLYALICYLIC STRUCTURE ELEMENT

CROSS-REFERENCE TO RELATED APPLICATIONS

This application claims priority to German Patent Application No. DE 10 2010 043 571.6 filed Nov. 8, 2010, and European Patent Application No. EP 11 188 086.0 filed Nov. 7, 2011, the entireties of which are incorporated herein by reference.

FIELD OF THE INVENTION

The present invention relates to certain novel polymerizable phosphoric acid derivatives (hereinafter referred to as monomers) comprising a polyalicyclic structure element, mixtures comprising one or a plurality of these compounds and corresponding curable blends and products as well as their respective use as a dental material or for the preparation of a dental material. The compounds are eminently suitable as bonding agents, in particular in dental adhesive materials. The invention further relates to a process for preparing these compounds or mixtures and a method for preparing a product, preferably a product suitable for dentistry.

BACKGROUND OF THE INVENTION

For a long while now, dental filling treatment has been determined by the use of amalgam. Since amalgam does not have an inherent adhesion to the hard dental material, the filling material must be applied mechanically, for example by preparing undercuts or blocking during the definitive treatment of cavities to allow it to be retained and maintained in the cavity. Such a method requires an abundance of healthy hard dental material and no longer meets the current standard of restorative dentistry which calls for minimally invasive preparation and the most substance-friendly cavity design. Because amalgam does not demonstrate any inherent adhesion to the hard dental material, when amalgam is used a marginal gap always results between the preparation and the tooth filling material. In the weeks following the insertion of the filling, this marginal gap is extensively filled by bactericidal corrosion products of the amalgam and other deposits and the ingress of cariogenic germs is effectively prevented. The larger the marginal gap, the smaller the proportion of amalgam corrosion products in the gap and so the ingress of bacteria is increasingly more likely. A wide marginal gap leads to a rapid colonization by microorganisms, which can lead to the formation of secondary caries and thus to the loss of the filling. In addition, amalgam is considered to be toxicologically dangerous and from the aesthetic point of view is thoroughly unsatisfactory.

These are major reasons why an increasing number of patients favor tooth-colored synthetic materials or other alternatives to amalgam for filling their cavities.

The advent of curable, plastic synthetic materials as alternative filling materials in conservative dentistry brought with it a number of new problem areas which to date have not yet been satisfactorily resolved. The weaknesses of plastic filling synthetic materials include, apart from excess wear and biocompatibility, the so-called polymerization shrinkage and the problem of the durable, marginal gap-free bonding with the hard dental material which frequently jeopardizes the stability of the restoration.

When synthetic materials are cured, then during the transition from the liquid to the solid phase a change in density takes place. This phenomenon, also referred to as shrinkage, can lead to the formation of a durable and stable bond between the tooth structure and the filling material not being possible since due to the polymerization shrinkage there are high tensile forces acting on the synthetic material—tooth structure bond. This effect can also be further complicated by opposing swelling effects taking place at different times due to the absorption of oral fluids. The absorption of fluids from the oral cavity is primarily determined by the polarity of the synthetic material components of the filling and of the adhesive. High polar materials tend to absorb larger quantities of water from the saliva leading to an increase in volume and to a gradual detachment of the synthetic material from the hard dental material. The moisture absorbed can also trigger hydrolytic processes, which often involve organic or inorganic-organic esters and can lead to a considerable weakening of the bond and the physical characteristics of the filling, which can then have an adverse effect on the long-term prognoses for stability. If the filling material does not have sufficient adhesion to the edge of the cavity then marginal gaps form between the tooth and the restoration which are frequently responsible for hypersensitivity and allow the ingress of liquids and bacteria to the dentin-synthetic material interface along the cavity wall at the bottom. Such insufficient edge adaptation of the dental filling composite can thus cause a bacterial undermining of the restoration with subsequent secondary caries formation and serious damage to the tooth. The consequences can range from marginal discoloration through irritation of the pulp to marking of the teeth and sepsis of the tooth root, which ultimately can lead to loss of the restoration and possibly of the tooth.

Progress in the method of adhesive bonding of filling materials to the hard tooth tissue has in the past been very gradual and is described in the literature.

One reason for the inadequate bond between the tooth structure and the synthetic material can be found in the structure of the dentin, which as a result of osmotic pressure in the direction of the oral cavity of the dentin liquor in the dentin tubules always has a certain humidity. Furthermore, the dentin consists to a large extent of organic substances, in particular collagen, in which the inorganic hydroxylapatite crystals are embedded. This type of structure has a much more complex make-up than tooth enamel. In addition, during preparation, a smear layer forms on the dentin which consists of components of the hard tooth substance, bacteria, saliva and blood and which cannot be removed either mechanically or by flushing.

These conditions make the creation of a durable bond between tooth structure and synthetic material quite considerably more difficult.

An initial consideration led to the use of surface-active monomers as bonding agents between the hydrophilic tooth structure and the hydrophobic synthetic filling. U.S. Pat. No. 3,200,142 proposed the addition product between the amino acid N-phenylglycin and glycidyl methacrylate (NPG-GMA) as a means of improving the adhesive bonding. The one resultant carboxylic acid function of N-(2-hydroxy-3-methacryloxypropyl)-N-phenylglycin, as a functional group is claimed to create a bond with the calcium ions of the hydroxyapatite contained in the inorganic component of the dentin, while the ethylenic double bond of the methacrylate group is claimed to ensure a covalent bond with the synthetic filling material during polymerization. The addition product is claimed to be particularly effective in its carboxylic acid salt form.

In similar approaches monomeric bonding agents were used which apart from the carboxylic acid function (or a group that can be converted to a carboxylic acid function), can contain other surface-active structure units such as phosphate, sulfate, sulfinate, hydroxyl and amide groups.

An alternative approach for creating a marginal gap-free bond between the synthetic filling and the tooth structure consisted of formulating bonding systems able to react with the organic constituents of the dentin, the collagen and a resultant group of the bonding agent. Use has been made here, by way of example, of compounds having aldehyde groups such as for example glutaraldehyde (EP 0141324). The aldehydes function is, for example, claimed to react with an amino function of the protein in the collagen in a first step to form an amino alcohol, in order then in the second step to react to form a Schiff base with the separation of water. It has further been proposed to use the aldehyde groups-containing compounds together with monomers provided with active hydrogen atoms such as hydroxyethyl methacrylate, in order to ensure that the elimination of water and thus the reaction in the second step and the coupling of the bonding monomer to the dentin actually takes place, because Schiff bases may not be sufficiently stable under the aqueous conditions of the oral cavity.

In addition to the aldehydes reaction, attempts have been made at a targeted grafting of the collagen through tri-n-butylborane initiated grafting-copolymerization (U.S. Pat. No. 4,830,616).

A further refinement of the system is described in DE 4137076. Instead of compounds with aldehydes groups, here β-dicarbonyl compounds, such as for example 2-acetoacetoxyethyl methacrylate, are used. It was assumed that the β-carbonyl function has a considerably higher reactivity to the protein, i.e. the collagen, compared to the aldehyde group and that in addition the complexing characteristics of the β-carbonyl group have a role to play.

Attempts have also been made through a combination of strategies to prepare adhesive compositions which bind to both collagen and calcium (EP 0321683).

In practice, however, it has transpired that the coefficients of adhesion of the abovementioned system drop considerably after a short time. In the further course of efforts to develop suitable and reliable adhesive monomers, finally a very limited number of quite special compounds were found that have a high adhesion between the tooth structure and the filling material even after ageing of the system. These compounds were then also used in dental materials and sold commercially. These current bonding agents require various processing methods in order to successfully bind with hard dental materials. What they all have in common is an alteration of the enamel or dentin by acids, primers or conditioners, the task of which is, put simply, to roughen the surface by creating a retentive pattern. This etching takes place usually in a separate step. Liquid nonpolar resin mixtures can then, frequently through the intermediary of polar, volatile solvents, infiltrate the retentive surfaces and cure. The acids, primers and conditioners used often contain organic or inorganic acids such as for example phosphoric acid or citric acid, which because of their low pH values dissolve the inorganic constituents over a certain time and must then be removed. In other modern bond materials the etching of the bonding base is combined with the application of the adhesive by using bonding-promoting, acid and polymerizable compounds.

One compound from the group of mono- or diphosphate esters of hydroxyalkyl methacrylate that mediates in bonding has proven to be 10-(meth)acryloyloxydecyl dihydrogen phosphate (10-MDP) (EP 0074708, EP 1084131). The phosphoric acid function forms with the hydroxyl apatite stable, water-insoluble salts wherein calcium is complexed by means of the phosphoric acid groups. The methyl spacer appears to have an accurately tailored length for avoiding mutual interference from steric affects during bond formation at both ends of the bonding agent. In turn, this seems to be a prerequisite for being able to wet the substrate surface in an optimum and even manner.

In terms of its preparation 10-MDP can be obtained by reacting 10-hydroxydecyl(meth)acrylate with phosphorous oxychloride.

Within the context of the present text (meth)acrylic means both acrylic and methacrylic.

Further compounds of this type are, by way of example 2-(meth)acryloyloxyethyl dihydrogen phosphate, 6-(meth)acryloyloxyhexyl dihydrogen phosphate, 4-(meth)acryloyloxybutyl dihydrogen phosphate, 8-(meth)acryloyloxyoctyl dihydrogen phosphate, 2-(meth)acryloyloxynonyl dihydrogen phosphate, 11-(meth)acryloyloxyundecyl dihydrogen phosphate, 20-(meth)acryloyloxyeicosyl dihydrogen phosphate, 1,3-di(meth)acyloyloxypropyl-2-dihydrogen phosphate or 2-(meth)acryloyloxyethylphenyl dihydrogen phosphate.

Instead of a phosphoric acid radical the polymerizable monomers can also have a diphosphoric acid radical, such as for example di(2-(meth)acryloyloxyethyl)pyrophosphate, di(2-(meth)acryloyloxypropyl)pyrophosphate, di(2-(meth)acryloyloxybutyl)pyrophosphate, di(2-(meth)acryloyloxypentyl)pyrophosphate, di(2-(meth)acryloyloxyhexyl)pyrophosphate, di(2-(meth)acryloyloxydecyl)pyrophosphate, etc. The corresponding acid halogenides can also be used.

Apart from polymerizable monomers with a phosphoric acid or pyrophosphoric acid radical, corresponding compounds can be used which have a phosphonic acid, a thiophosphonic acid or a sulfonic acid radical.

Similarly, monomers that mediate in bonding can for example be synthesized from hydroxyalkyl methacrylate or glyceryl dimethacrylate. Thus for example during the reaction of hydroxyethyl methacrylate with phosphoroxychloride blends arise having mono-, di-, and triesters.

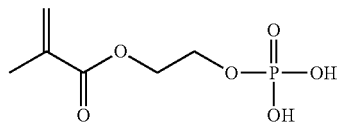

Monoester of phosphoric acid

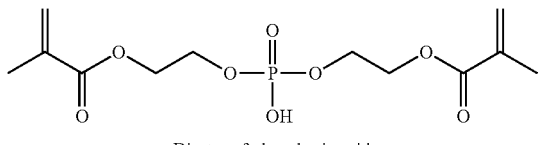

Diester of phosphoric acid

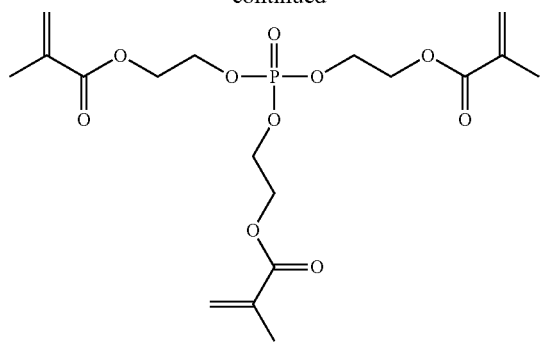

Triester of phosphoric acid

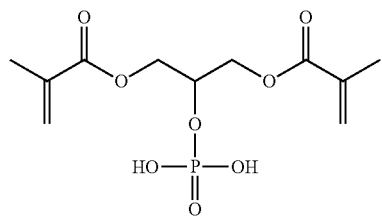

Glyceryl dimethacrylate phosphate

A further type of adhesive monomer is the phosphoric acid ester of pentaerythritol triacrylate or of dipentaerythritol pentaacrylate (PENTA, U.S. Pat. No. 4,514,342). The ester is prepared from dipentaerythritol monohydroxy pentaacrylate and phosphoroxy chloride in the presence of triethyl amine.

Other compounds mediating in bonding are methacryloyloxyalkyl derivates of aromatic carboxylic acids. It has transpired that trimellitic acid-4-methacryloyloxyethylester (4-MET) or 4-methacryloxy-ethyl trimellitate anhydride (4-META) in particular can be used as a bond promoting monomer (DE 2828381, U.S. Pat. No. 4,148,988, EP 0684033, EP 0684034). 4-META is preparable by a dehydrochlorination reaction between hydroxyethyl methacrylate and anhydrous trimellitic acid chloride or by a dehydration reaction between 2-hydroxyethyl methacrylate and trimellitic acid anhydride.

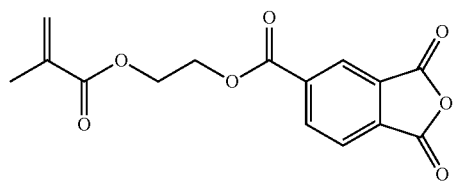

4-META

Similarly pyromellitic acid dimethacrylate and pyromellitic acid glycerol dimethacrylate are likewise claimed to be suitable adhesive monomers.

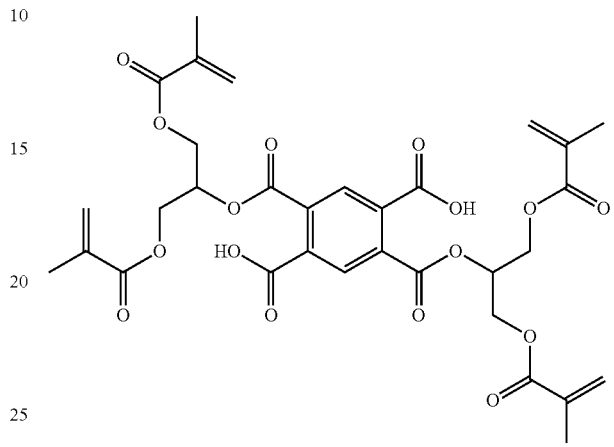

Pyromellitic acid dimethacrylate

Pyromellitic acid (bis)glycerol dimethacrylate

Other methacryloyloxyethyl derivates of aromatic carboxylic acids, that are claimed to be suitable as adhesive monomers, are corresponding compounds of the phthalic acid.

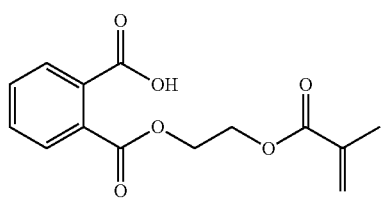

Methacryloyloxyethyl phthalate

Methacryloxyethyl derivates of succinic acid and maleic acid are also claimed to be usable as adhesive monomers.

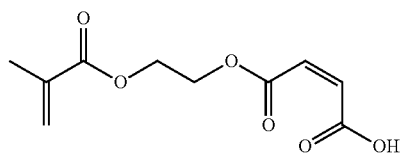

Methacryloyloxyethyl maleate

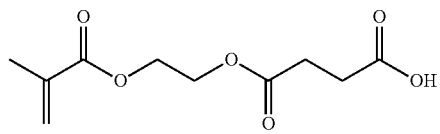

Methacryloyloxyethyl succinate

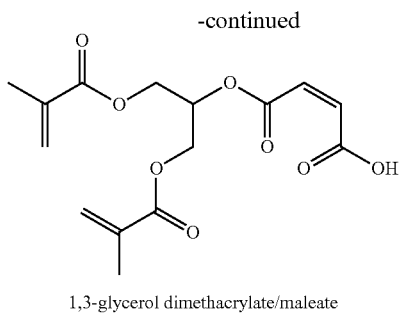

1,3-glycerol dimethacrylate/maleate

Further reactive adhesive components are disclosed in EP 1148060, EP 0909761 and EP 1148071, where polymerizable and hydrolitically stable acrylophosphonic acids are described. The complicated synthesis route begins with the reaction of formaldehyde and a suitable acrylic acid ester in the presence of a catalyst with the formation of a methyl group in the α-position of the ester and subsequent halogenisation of the alcohol with an inorganic acid halogenide. The α-halogen methacrylic acid ester prepared in this way is then reacted with suitable and previously protected mono- or difunctional phosphonic acid esters. After separation of the protective group the polymerizable and hydrolytically-stable acrylic-phosphonic acid is obtained, the feature of which is the resultant oxo-ethyl acrylic function.

In EP 1346717 tetramethacryloxyethyl pyrophosphate is described as a bond-mediating substance. It is claimed that the pyrophosphate breaks up under the aqueous conditions and is hydrolyzed to form phosphoric acid esters, which initially it is claimed ensure a very low pH value and then help to etch the hydroxyl apatite. It is claimed that the phosphoric acid radicals are neutralized by calcium ions escaping from the dentin thus forming a cement-like bond with the tooth, while the methacrylate groups are able to react with the tooth filling material through photopolymerization.

In EP 1721949 A1 polymerizable derivatives of ethylenediaminetetraaectic acid are proposed as bonding agents in dental adhesive materials. There the bond-mediating effect of for example di-oxyethoxymethacrylic acid ethylendiaminetetraaxcetic acid ester was demonstrated.

Curable monomers comprising a polyalicyclic structure element are essentially known and are used in various applications, such as dental engineering.

EP 1238993 describes a method for producing polyisocyanates containing acyl urea groups and blends of these and their use as starting components for preparing polyurethane synthetic materials.

EP 0611752 A1 discloses a method for preparing olefinically unsaturated isocyanates containing urethane groups while maintaining a certain NCO/OH equivalent ratio. The isocyanates that can be obtained according to EP 0611752 A1 can be used as binding agents for coating materials to be used at room temperature in single component form.

EP 0209700 A2 and DE 3522005 describe (meth)acrylic acid derivatives of certain tricyclodecenes with divalent bridge members from the group of urethanes or ureas, which can be used in the area of dentistry.

DE 102004060285 A1 relates to radiation-curable compounds based on a dicidol mixture (containing two or three isomers 3,8-, 4,8- and/or 5,8-bis(hydroxymethyl)tricyclo[5.2.1.0$^{2,6}$]decane) with at least one compound, having at least one ethylenically unsaturated grouping with simultaneously at least one reactive grouping in relation to dicidol, wherein this compound may be a reaction product of hydroxyalkyl(meth)acrylate and diisocyanate. The compositions according to DE 102004060285A1 can be used as radiation-induced-curing coating materials, adhesives, laminations, printing and other inks, polishes, varnishes, pigment pastes, fillers, cosmetic materials, packaging materials and/or sealing and/or insulating materials.

WO 2006/063891 A1 discloses radically polymerizable compounds, substantially containing the reaction product of a dicidol mixture and at least one compound, which has at least one ethylenically unsaturated grouping with simultaneously at least one reactive grouping in relation to dicidol. The areas of application correspond to those mentioned in DE102004060285 A1.

U.S. Pat. No. 6,670,499 B1 describes diurethanes derived from adamantane. The compounds described in U.S. Pat. No. 6,670,499 are suitable as intermediate products for use in dentistry or for producing optical materials (such as lenses, for example).

U.S. Pat. No. 6,794,528 B2 describes phosphoric acid esters with polialicyclic structure elements. The compounds disclosed in U.S. Pat. No. 6,794,528 B2 are highly heat-resistant and suitable for use as flame retardants and as plasticizers or stabilizers. These compounds in particular have no curable functionalities.

JP 2007091642A discloses compounds according to the following formulas

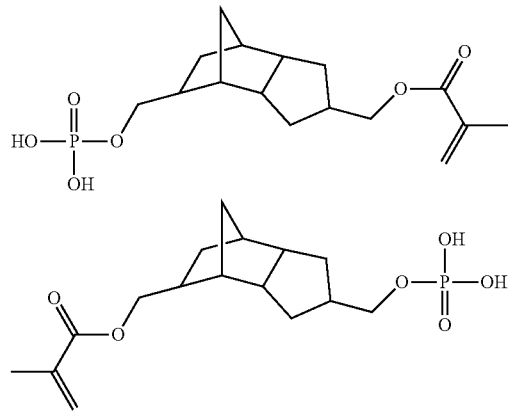

The compounds, products and methods disclosed in JP 2007/091642A are not the subject-matter of the present invention.

DE 3205030 A1 discloses phosphate derivatives and their application for the preparation of fillers for, for example, teeth. Many of the phosphate derivatives disclosed comprise an acryloyloxy group or methacryloyloxy group. The compounds, products and methods disclosed in DE 3205030 A1 are not the subject-matter of the present invention. DE 60312714 T2 discloses self-etching, self-priming single-component dental adhesive compositions comprising a polymerizable acidic phosphoric acid ester monomer of a formula (A). In certain configurations the phosphoric acid ester monomer of formula (A) can comprise selected polyalicyclic structure elements. In a similar way US 2006/0246017 A1 discloses a polymerizable acidic phosphoric acid ester monomer of a formula (A) for application as a self-priming, self-etching adhesive. The compounds, products and methods disclosed in DE 60312714 T2 and US 2006/0246017 A1 are not the subject-matter of the present invention.

In the area of dental engineering and for various other application there is a constant need for further polymerizable monomers. There is in particular a need for monomers which allow the production of products and polymers with improved characteristics.

DESCRIPTION OF THE INVENTION

The primary object of the invention is to provide novel polymerizable monomers which are particularly suitable for applications in dental engineering, although without being limited to this are of use. These new polymerizable monomers should be bond-promoting monomers (also known as bonding agents), i.e. they should have a good adhesion, preferably to solid surfaces, in particular in relation to the hard dental material.

Here these monomers should in products in the cured state preferably have a better adhesion to a surface, preferably to hard dental material, here preferably dentin, than trimellitic acid anhydride-4-methacryloylox ethyl ester (4-META), more preferably a coefficient of adhesion of at least 12.5 MPa.

The adhesive bonding of composites with hard dental material is generally achieved by using the total-etch method or primers, which prepare the surfaces of the tooth to receive adhesive resins. The concentrated phosphoric acid used in the total-etch method should, through the partial dissolution of enamel and dentin and opening up of the dentin pores, ensure the inflow of the bonding adhesive and through the enamel etching pattern increasing retentive anchoring. This etching with phosphoric acid is an additional working step in restorative filling treatment, which is both involved and relatively prone to failure. Leaving the etching agent to work for too long or too short a time leads to problems with the bond and insufficient removal often causes lengthy problems with the pulp and hypersensitivity. Other bonding systems require primers, which modify the cavity surfaces and require length processing of the actual adhesive resin prior to use. Newer dental adhesives work not according to the total-etch method but according to the so-called non-etch method and are self-conditioning. Such preparations are substantially easier, more secure in use and are less time-consuming to handle.

The new polymerizable monomers should preferably also be usable in the non-etch method and bring about the dentin modification necessary for the bonding procedure, i.e. without the need for a separate etching step by acid and without the use of primers.

The new polymerizable monomers should also provide and adhesion-promoting effect as a constituent of dental filling composites and fixing cements, underfilling materials, flow materials, crack sealants, lacquers, root canal materials, stump build-up materials and temporary restoration materials (inlays, onlays, crowns, bridges, fixing materials).

In the area of dental engineering dental polymers are subject to particular requirements, such as for example good biocompatibility, low toxicity of the monomer (in the event that it does not polymerize, but remains in part as a monomer in the polymer matrix), a lower residual monomer content, etc.

The monomers should also preferably have a high biocompatibility and high strength. The monomers sought should furthermore preferably be simple to prepare and easy to process.

But the polymers obtainable using the monomers according to the invention should preferably create a stable and strong bond between the hard dental material and the dental functional material and for example ensure as a bonding in the case of a filling composite a marginal gap-free sealing of the cavity.

These problems are solved by a compound of the structure $$(HO)_w—P(=O)-[G-(L)_x-Q(YZ)_b]_y,$$

wherein here and below the following applies:
each Q, independently of any other groups Q, represents a saturated or olefinically unsaturated polyalicyclic structure element selected from the group consisting of bicyclic, tricyclic, tetracyclic, pentacyclic and hexacyclic hydrocarbon radicals, wherein Q carries no further substituents or one or more substituents selected from the group consisting of alkyl groups (here preferably C1-C4-alkyl), alkoxy groups (here preferably C1-C4-alkoxy), halogen atoms (here preferably F) and trifluormethyl groups,
index b is an integer selected from the group of integers 1, 2 and 3,
each Z represents a structure element, which independently of any further structure elements Z is selected from the group consisting of

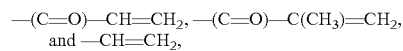

each Y represents a structure element, which—independently of any other structure elements Y—contains one or more N-atoms and the polyalicyclic structure element Q binds with Z in such a way that the chain of atoms binding Q with Z contains one or more N atoms,
each structure element G, independently of any further structure elements G, represents either O or NH,
each L represents a structure element which, independently of any further structure elements L, binds the group G with the polyalicyclic structure element Q,
the index w is selected from the group of integers 0, 1 and 2,
each index x independently of any further indices x represents either 0 or 1,
the index y is selected from the group of integers 1, 2 and 3, wherein the total of w+y=3.

The monomers according to the invention are in particular suitable for applications in dentistry and have a good adhesion, particularly to the hard dental material.

The monomers according to the invention, in the cured state in products, have a very good adhesion to solid surfaces, preferably to dentin, in the latter case a coefficient of adhesion of at least 12.5 MPa.

The compounds according to the invention are suitable as additives for and as a constituent of bond-improving adhesive(s), in particular for mineral substrates and in particular hard dental materials. They also allow application in the non-etch method, since the compounds according to the invention, including in combination with one or a plurality of further monomers, evidently bring about the dentin modification necessary for the bonding procedure.

The compounds according to the invention also demonstrate a bond-improving effect as a constituent of dental filling composites and fixing cements, underfilling materials, flow materials, crack sealants, lacquers, root canal materials, stump build-up materials and temporary restoration materials (in particular inlays, onlays, crowns, bridges and/or fixing materials).

In preferred compounds according to the invention Y, independently of any further structure elements Y, is selected from the group consisting of linear, branched or ring-comprising divalent organic bridge members with 1 through 20 C atoms, preferably with 1 through 12 C atoms, preferably with 1 through 8 C atoms, and optionally 1 through 6 heteroatoms, preferably 1 through 5 heteroatoms, wherein the heteroatoms that are optionally present are preferably selected from the group consisting of N and O.

Preferred compounds according to the invention have the following structure

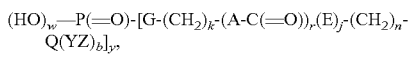

wherein the following applies:
- each index k is an integer that, independently of any further indices k, is selected from the group of integers 0 through 12, preferably from the group of integers 0 through 8.
- each structure element A, independently of any further structure elements A, represents either O or NH,
- each structure element E, independently of any further structure elements E, represents either O or NH,
- each index r independently of any further indices r represents either 0 or 1,
- each index j independently of any further indices j represents either 0 or 1,
- each index n independently of any further indices n represents either 0 or 1, wherein if k=0, the index j represents 0 and the index r represents 0.

In a preferred configuration the index k represents 0 or k represents 2.

In a preferred configuration the index n represents 1.

In a preferred configuration the structure element E represents oxygen.

In the event that y>1, i.e. if y=2 or 3, in a preferred configuration the y radicals -[G-(CH$_2$)$_k$-(A-C(=O))$_r$-(E)$_j$-(CH$_2$)$_n$ -Q(YZ)$_b$] of a compound according to the invention are identical.

The "polyalicyclic" structure element Q is a bicyclic, tricyclic, tetracyclic, pentacyclic or hexacyclic hydrocarbon radical as defined above. The designations "bicyclic", "tricyclic", "tetracyclic", "pentacyclic" and "hexacyclic" here correspond to the IUPAC nomenclature.

A monomer according to the invention comprises at least one polyalicyclic structure element Q, derived from a corresponding polyalicyclic hydrocarbon. In the context of the present text, this means that b hydrogen atoms of the hydrocarbon are replaced by substituents YZ (as described above), and optionally one, two or a plurality of the hydrogen atoms not substituted by substituents YZ are substituted by alkyl groups, alkoxy groups, halogen atoms or trifluoromethyl groups.

The structure of unsubstituted bicycles is as follows:

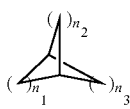

wherein $n_1$, $n_2$ and $n_3$ in each case independently or one another can represent an integer from 1 through 8, preferably an integer from 1 through 4.

The following examples are provided:

| | |
|---|---|
| For $n_1 = n_2 = 1$; $n_3 = 2$ | bicyclo[2.1.1]hexane |
| for $n_1 = 1$; $n_2 = n_3 = 2$ | bicyclo[2.2.1]heptane |
| for $n_1 = n_2 = 1$; $n_3 = 3$ | bicyclo[3.1.1]heptane |
| for $n_1 = n_2 = n_3 = 2$ | bicyclo[2.2.2]octane |
| for $n_1 = n_2 = 1$; $n_3 = 4$ | bicyclo[4.1.1]octane |
| for $n_1 = 1$; $n_2 = 2$; $n_3 = 3$ | bicyclo[3.2.1]octane |
| for $n_1 = 1$; $n_2 = 2$; $n_3 = 4$ | bicyclo[4.2.1]nonane |
| for $n_1 = n_2 = 2$; $n_3 = 4$ | bicyclo[4.2.2]decane |

A number of examples of disubstituted bicycles are shown below:

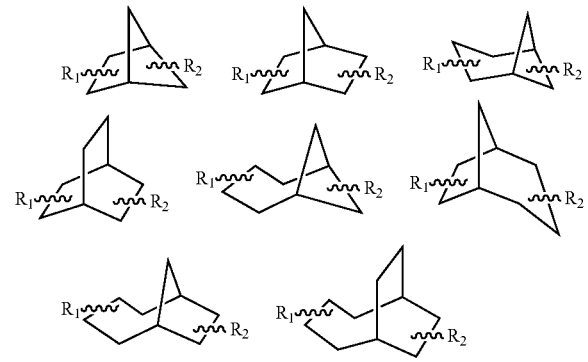

wherein R1 and R2 in each case represent the other radicals of the compound.

Examples of bicyclic structure elements Q are the bicyclo[1.1.1]pentane, bicyclo[2.1.1]hexane, bicyclo[2.2.1]heptane, bicyclo[3.1.1]heptane, bicyclo[2.2.2]octane, bicyclo[4.1.1]octane, bicyclo[3.2.1]octane, bicyclo[4.2.1]nonane, bicyclo[3.3.1]nonane, bicyclo[5.1.1]nonane, bicyclo[3.2.2]nonane, bicyclo[6.1.1]decane, bicyclo[5.2.1]decane, bicyclo[4.2.2]decane, bicyclo[3.3.2]decane, bicyclo[7.1.1]undecane, bicyclo[6.2.1]undecane, bicyclo[5.2.2]undecane, bicyclo[4.3.2]undecane, bicyclo[3.3.3]undecane, bicyclo[8.1.1]dodecane, bicyclo[7.2.1]dodecane, bicyclo[6.2.2]dodecane, bicyclo[5.3.2]dodecane, bicyclo[4.3.3]dodecane, bicyclo[4.4.2]dodecane, bicyclo[5.4.1]dodecane structure elements and even higher structure elements such as the corresponding tridecanes, tetradecanes, pentadecanes, etc.

For unsubstituted tricycles the following structures are possible:

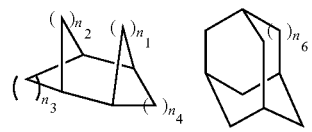

wherein $n_1$, $n_2$, $n_3$, $n_4$ or $n_6$ in each case independently of one another can represent an integer from 0 through 5.

The following examples are provided:

| | |
|---|---|
| For $n_1 = 2$; $n_2 = 0$; $n_3 = 2$; $n_4 = 3$ | tricyclo[4.3.2.0$^{2,5}$]undecane |
| for $n_1 = 0$; $n_2 = 1$; $n_3 = 2$; $n_4 = 3$ | tricyclo[5.2.1.0$^{2,6}$]decane |
| for $n_1 = 0$; $n_2 = 2$; $n_3 = 2$; $n_4 = 3$ | tricyclo[5.2.2.0$^{2,6}$]undecane |
| for $n_1 = 2$; $n_2 = 0$; $n_3 = 2$; $n_4 = 2$ | tricyclo[4.2.2.0$^{2,5}$]decane |
| for $n_6 = 1$ | tricyclo[3.3.1.1$^{3,7}$]decane |

In the following examples of single-, di- or tri-substituted tricycles are shown:

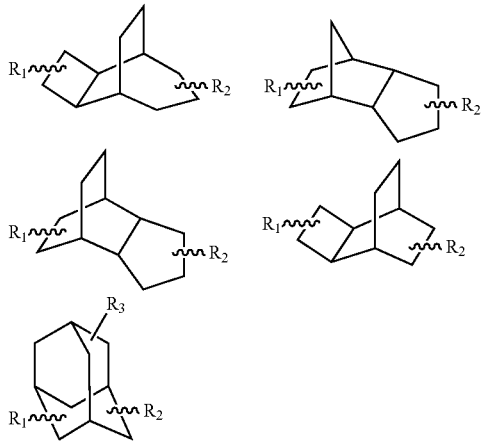

wherein R1, R2 and R3 in each case represent the other radicals of the compound.

Examples of tricyclic structure elements Q are the tricyclo[3.2.1.0$^{2,6}$]octane, tricyclo[4.2.1.0$^{2,6}$]nonane, tricyclo[5.2.1.0$^{2,6}$]decane, tricyclo[6.2.1.0$^{2,6}$]undecane, tricyclo[7.2.1.0$^{2,6}$]dodecane, or tricyclo[4.2.1.1$^{2,5}$]decane, tricyclo[4.3.1.1$^{2,5}$]decane, tricyclo[4.4.1.1$^{2,5}$]decane, tricyclo[2.2.1.0$^{2,6}$]heptane, tricyclo[2.2.2.0$^{2,6}$]octane, tricyclo[3.2.2.0$^{2,6}$]nonane, tricyclo[3.3.1.1$^{3,6}$]decane, tricyclo[3.2.1.1$^{3,7}$]nonane, tricyclo[4.2.2.2$^{2,5}$]dodecane, tricyclo[4.3.2.2$^{2,5}$]tridecane, tricyclo[4.4.2.2$^{2,5}$]tetradecane, tricyclo[4.2.1.0$^{3,7}$]nonane, tricyclo[4.4.1.1$^{1,5}$]dodecane, tricyclo[6.2.1.0$^{2,7}$]undecane, tricyclo[5.2.2.0$^{2,6}$]undecane, tricyclo[6.2.2.0$^{2,7}$]dodecane, tricyclo[4.3.2.0$^{2,5}$]undecane, tricyclo[4.2.2.0$^{2,5}$]decane or the tricyclo[5.5.1.0$^{3,11}$]tridecane structure element.

The following is a possible example for unsubstituted tetracycles:

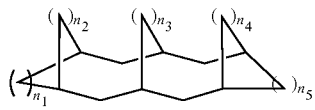

wherein $n_1$, $n_2$, $n_3$, $n_4$, and $n_5$ in each case independently of one another can represent an integer from 1 through 5.

The following examples are provided:

| | |
|---|---|
| For $n_1 = n_2 = n_3 = n_4 = 2$; $n_5 = 5$ | tetracyclo[9.6.2$^{3,9}$.2$^{13,16}$]tricosane |
| for $n_1 = n_5 = 2$; $n_2 = n_3 = n_4 = 1$ | tetracyclo[6.6.1$^{3,6}$.1$^{10,13}$]heptadecane |
| for $n_1 = n_2 = n_3 = n_4 = n_5 = 2$ | tetracyclo[6.6.2$^{3,6}$.2$^{10,13}$]eicosane |

A number of examples of disubstituted tetracycles are shown below:

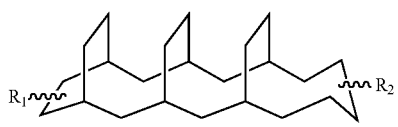

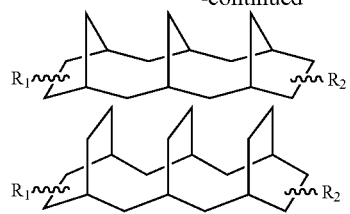

wherein R1 and R2 in each case represent the other radicals of the compound.

Examples of tetracyclic structure elements Q are the tetracyclo[4.4.2.2$^{2,5}$.1$^{7,10}$]pentadecane, tetracyclo[5.5.2.2$^{2,6}$.1$^{8,12}$]heptadecane, tetracyclo[6.6.2.2$^{2,7}$.1$^{9,14}$]nonadecane, tetracyclo[4.4.2.2$^{2,5}$.2$^{7,10}$]hexadecane, tetracyclo[5.4.2.2$^{2,6}$.1$^{8,11}$]hexadecane, tetracyclo[6.2.1.1$^{3,6}$.0$^{2,7}$]dodecane, tetracyclo[9.6.2$^{3,9}$.2$^{13,16}$]tricosane-, tetracyclo[9.6.2$^{3,9}$.2$^{13,16}$]tricosane-, tetracyclo[6.6.1$^{3,6}$.1$^{10,13}$]heptadecane, tetracyclo[6.6.2$^{3,6}$.2$^{10,13}$]cosane, or tetracyclo[5.3.2.1$^{2,4}$.0$^{3,6}$]tridecane structure element.

Examples of pentacyclic structure elements Q are the pentacyclo[4.2.0.0$^{2,5}$.0$^{3,8}$.0$^{4,7}$]octane, pentacyclo[13.7.4.3$^{3,8}$.0$^{18,20}$.1$^{13,28}$]triacontane, pentacyclo[8.6.6.5$^{2,9}$.1$^{23,26}$]octacosane or pentacyclo[3.3.0.0$^{2,4}$.0$^{3,7}$.0$^{6,8}$]octane structure element.

An example of a hexacyclic structure element Q is the hexacyclo[15.3.2.2$^{3,7}$.1$^{2,12}$.0$^{11,25}$]pentacosane.

Preferred compounds that are suitable for preparing the monomers according to the invention are for example:

Alcohol substituted polyalicyclic hydrocarbons:
bicycle(2.2.1)heptan-2.7-diol,
[5-(hydroxymethyl)-6-bicyclo[2.2.1]hept-2-enyl]-methanol,
tricyclo[3.3.1.1$^{3,7}$]decane-1,3-diethanol,
tetracyclo[6.3.0.0$^{2,6}$.0$^{5,9}$]undecane-3,11-diol,
[6-(hydroxymethyl)-6-bicyclo[2.2.1]hept-2-enyl]methanol,
tricyclo[3.3.1.1$^{3,7}$]decane-1,3-diol,
bis(hydroxymethyl)tricyclo[5.2.1.0$^{2,6}$]decane, etc.

Isocyanate substituted polyalicyclic hydrocarbons:
bis(2-isocyanatoethyl)-5-norbornene-2,3-dicarboxylate,
2,5(2,6)-bis(isocyanatomethyl)bicyclo[2.2.1]heptane,
bis(isocyanatomethyl)tricyclo[5.2.1.0$^{2,6}$]decane, etc.

Mixed or amino-substituted polyalicyclic hydrocarbons:
tricyclo[3.3.1.1$^{3,7}$]decan-1-ol-3-amino,
pentacyclo[4.4.0.0$^{2,5}$.0$^{3,8}$.0$^{4,7}$]nonane-2,4-diamine,
tricyclo[3.3.1.1$^{3,7}$]decan-1-ol-3-amino,
bis(aminomethyl)tricyclo[5.2.1.0$^{2,6}$]decane, etc.

In a preferred embodiment the structure of the polyalicyclic structure element Q is derived from a bicyclic[a.c.d] hydrocarbon. The letters a, c and d are integers and have the meaning of the IUPAC nomenclature. The total of a, c and d is preferably in the range 3 through 13, preferably in the range 4 through 7.

In a further preferred embodiment the structure of the polyalicyclic structure element is derived from a tricyclic [a.c.d.f]hydrocarbon. The total of a, c, d and f is preferably in the range 6 through 12, preferably in the range 7 through 9.

In a preferred embodiment the structure of the polyalicyclic structure element is derived from a tricyclic[a.2.1.0$^{2,(a+1)}$]hydrocarbon, wherein a can in each case represent 3, 4, 5, 6 or 7.

In a further preferred embodiment the structure of the polyalicyclic structure element is derived from a tricyclic [a.2.2.0$^{2,(a+1)}$]hydrocarbon, wherein a can in each case represent 3, 4, 5, 6 or 7.

In a further preferred embodiment the structure of the polyalicyclic structure element is derived from a tricyclic [a.3.1.1]hydrocarbon, wherein a can in each case represent 3, 4, 5, 6 or 7.

Preferred compounds according to the invention comprise one, two or a plurality of functional groups selected from the group consisting of
  esters,
  urethane,
  N-acyl urethane,
  urea,
  N-acyl urea
and
  amide, wherein the amide function is not directly linked with an N-atom, an O-atom or a carbonyl group.

From this it can be inferred that for compounds according to the invention, containing a special amide group (as defined), this amide group for example is not a component of the urethane or urea group.

A preferred amide group is (meth)acrylamide.

Preferred compounds according to the invention are characterized in that the grouping YZ comprises a functional group selected from the group consisting of esters, urethane, N-acyl urethane, urea, N-acyl urea and amide, wherein the amide function is not directly linked with an N-atom, an O-atom or a carbonyl group.

Further compounds preferred according to the invention are characterized in that the grouping YZ comprises a functional group selected from the group consisting of esters, urethane, N-acyl urethane, urea, N-acyl urea and methacrylamide. Preferably here, the grouping YZ contains a functional group selected from the group consisting of urethane, N-acyl urethane, urea, N-acyl urea and methacrylamide, where the or at least one of the N-atoms of this functional group is positioned in the chain of atoms linking Q with Z.

Preferred compounds according to the invention are those which contain no carbonate group, in particular those in which the structure element E and the structure element A do not both at the same time represent oxygen.

Preferred are compounds according to the invention in which
(i) the structure element Z represents $-(C=O)-C(CH_3)=CH_2$,
and/or
(ii) the functional groups are esters, urethane, urea or methacrylamide groups, since particularly good results have been achieved with these compounds,
and/or
(iii) the structure element Q represents a tricyclo$[5.2.1.0^{2,6}]$ decane radical.

Further preferred are compounds according to the invention, in which the structure element Z represents $-O-(C=O)-C(CH_3)=CH_2$, wherein the functional groups are esters, urethane or methacrylamide groups and the structure element Q represents a tricyclo$[5.2.1.0^{2,6}]$decane radical.

Preferred are compounds according to the invention in which all photocurable groups present correspond to the structure element Z.

A compound according to the invention, apart from photocurable groups of the structure element Z, can also comprise other polymerizable, preferably terminal polymerizable groups, which are not photocurable, in particular not under the normal conditions that exist in dentistry. This is generally not preferred, however, since such groups do not contribute towards the desired characteristics of the product that exists following polymerization.

Further preferred compounds are characterized in that the grouping YZ has a structure selected from the group consisting of $(-CH_2)_n-O-C(=O)-NH-Z$, $(-CH_2)_n-O-C(=O)-NH-(CH_2)_m-O-Z$, $(-CH_2)_n-NH-C(=O)-NH-Z$, $(-CH_2)_n-NH-C(=O)-NH-(CH_2)_m-O-Z$, $(-CH_2)_n-NH-Z$, and $(-CH_2)_n-NH-C(=O)-O-(CH_2)_m-O-Z$, wherein Z and n have the meaning given above and wherein the following also applies:
  each index m is an integer that, independently of any further indices m, is selected from the group of integers 1 through 12, preferably from the group of integers 2 through 8.

In a preferred configuration the index n represents 1.
In a preferred configuration the index m represents 2.

Preferred compounds according to the invention are those wherein Q represents a polyalicyclic structure element, preferably a saturated polyalicyclic structure element, selected from the group consisting of bicyclic or tricyclic hydrocarbon radicals, wherein preferably none of the hydrogen atoms of this polyalicyclic structure element Q not already substituted by substituents YZ or by the respective group comprising the structure element G-$(L)_x$ is substituted.

A preferred bicyclic hydrocarbon radical is a bicyclo [2.2.1]heptanes radical, i.e. according to the invention compounds are preferred that have a bicyclo[2.2.1]heptane (norbornan).

In a further preferred embodiment the structure of the polyalicyclic structure element Q is derived from a tricyclodecane or tricyclodecene hydrocarbon.

Particularly preferred are monomers according to the invention whose polyalicylic structure element Q is derived from one of the following tricyclic hydrocarbons: tricyclo $[5.2.1.0^{2,6}]$decane (TCD), tricyclo$[5.2.1.0^{2,6}]$dec-3-ene or tricyclo$[3.3.1.1^{3,7}]$decane (adamantane), i.e. preferred are compounds according to the invention, which have a TCD structure, a tricyclo$[5.2.1.0^{2,6}]$dec-3-ene structure or an adamantane structure.

Particularly preferred compounds according to the invention are those wherein the structure element Q represents a tricyclo$[5.2.1.0^{2,6}]$decane radical, a tricyclo$[5.2.1.0^{2,6}]$dec-3-ene radical, a tricyclo$[3.3.1.1^{3,7}]$decane radical or a bicyclo [2.2.1]heptane radical.

The stated particularly preferred compounds according to the invention, in which the structure element Q represents a tricyclo$[5.2.1.0^{2,6}]$decane radical, a tricyclo$[5.2.1.0^{2,6}]$dec-3-ene radical, a tricyclo$[3.3.1.1^{3,7}]$decane radical or a bicyclo [2.2.1]heptane radical, are preferably those with a tricyclo $[5.2.1.0^{2,6}]$decane structure, a tricyclo$[5.2.1.0^{2,6}]$dec-3-ene structure, a tricyclo$[3.3.1.1^{3,7}]$decane structure or a bicyclo [2.2.1]heptane structure, in which none of the hydrogen atoms of this polyalicyclic structure element Q not substituted by substituents YZ is substituted.

The present invention further relates to a method for preparing a compound of the structure $(HO)_w-P(=O)-[G-(L)_x-Q(YZ)_b]_y$ or a mixture comprising at least one compound of structure $(HO)_w-P(=O)-[G-(L)_x-Q(YZ)_b]_y$, in each case preferably in one of the configurations identified above as preferred or particularly preferred, with the following steps:
(i) providing a compound HG-(L)$_x$-Q(YZ)$_b$,
(ii) reaction of the compound from step (i) with POCl$_3$ or phosphorous(V) oxide, preferably in the presence of an amine, preferably a tertiary amine,
(iii) hydrolysis of the reaction product formed in step (ii), wherein G, L, Q, Y, Z, w, x, b and y in each case have the above meanings, and
wherein the molar quantity of the compound from step (i) per atom equivalent of phosphorous is in the range 0.5 through 6, preferably in the range 0.6 through 5, preferably in the range 0.7 through 4, more preferably in the range 0.8 through 3.5.

Phosphorous(V) oxide is also known by the name phosphorous pentoxide and is frequently indicated by the formula P$_2$O$_5$, wherein phosphorous(V) oxide is more accurately described by the formula P$_4$O$_{10}$ (diphosphorous pentoxide).

The preparation of the compounds according to the invention is explained by way of example using the following reaction schemes.

The method steps 1. ii) or 2.) iii) relate here to step ii) (reaction of the compound from step (i) with POCL$_3$ or phosphorous(V) oxide) or iii) (hydrolysis of the reaction product formed in step (ii)) of a preparation method according to the invention.

Here in scheme 1 and scheme 2 in each case:
Q, n, Z, G, k, w and y have the meaning given above,
R is a structure element that binds the OCN group with the structure element Z, preferably R is a group —(CH$_2$)$_m$—O, wherein m has the meaning indicated above,
the q, independently of any further indices q, represents either 0 or 1.

Scheme 1: Synthesis route for preparing the compounds according to the invention starting with a polyalicyclic diol

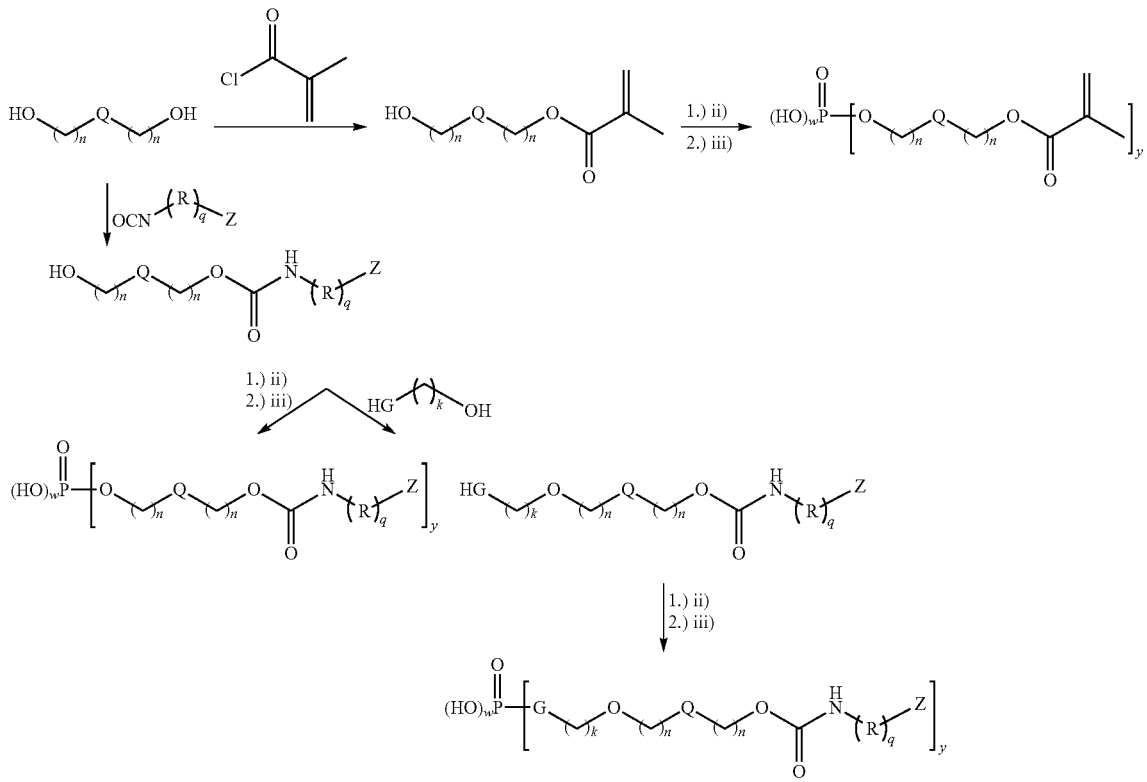

Scheme 2: Synthesis route for preparing the compounds according to the invention starting with a polyalicyclic diamine.

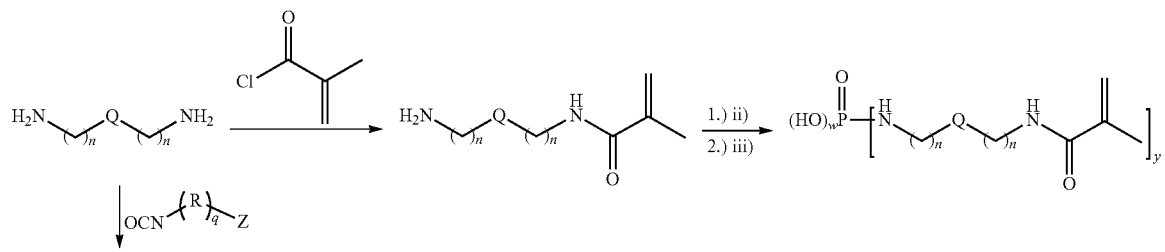

-continued

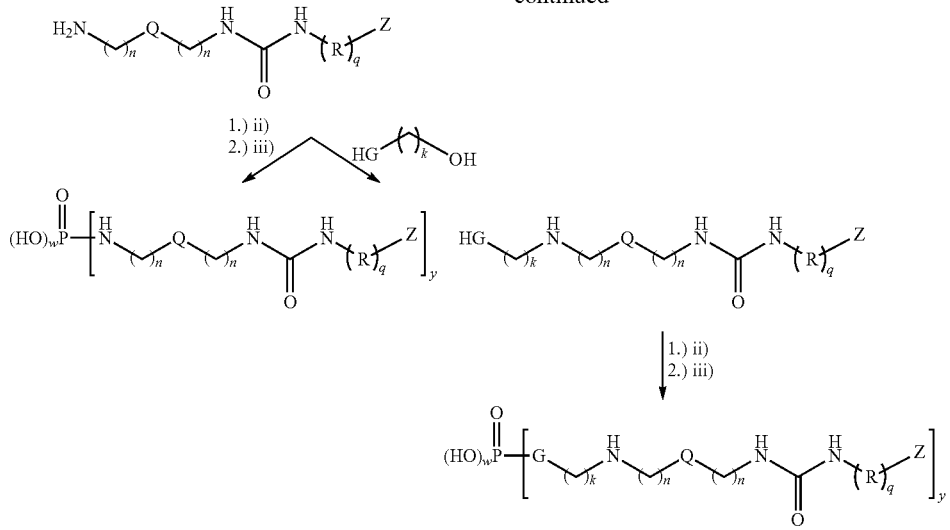

Scheme 3: Synthesis route for preparing the compounds according to the invention starting with a polyalicyclic diisocyanate

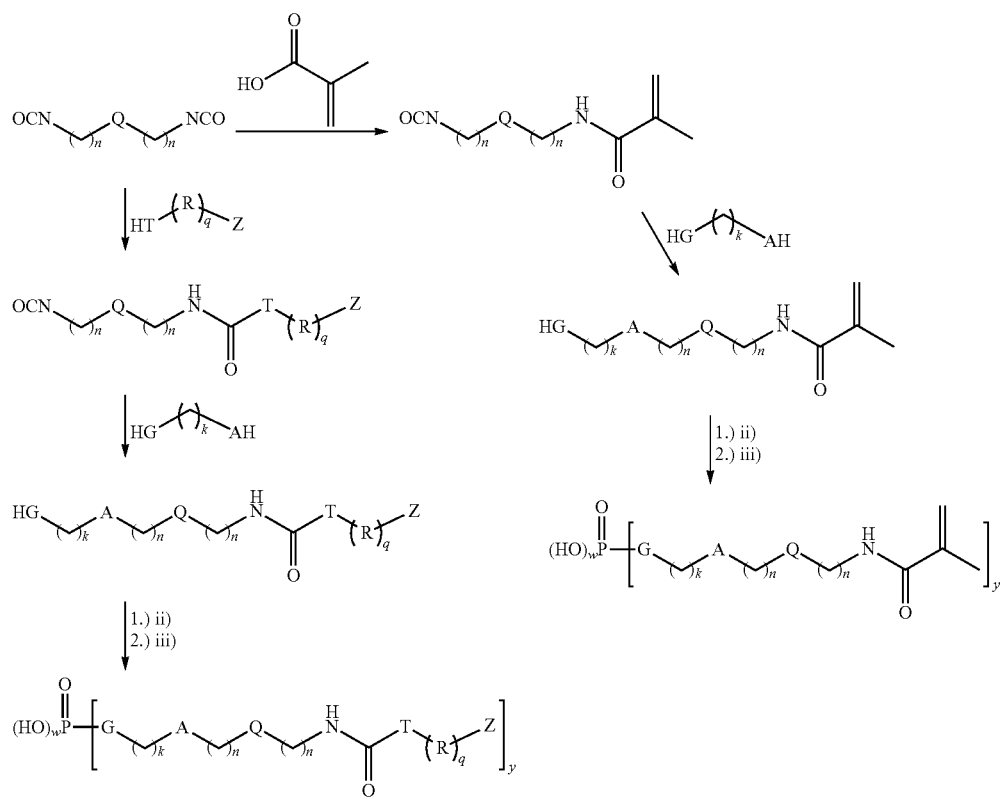

wherein Q, n, Z, G, A, k, w, y, R and q have the meaning given above and each structure element T, independently of any further structure elements T, represents either O or NH.

The statements above or below relating to the compounds according to the invention identified as preferred and particularly preferred apply to the preferred and particularly preferred configurations of the method, mixtures, blends, products and applications according to the invention accordingly in each case.

In a further aspect the present invention relates to a mixture comprising one, two or a plurality of different compounds according to the invention that are preparable preferably using a method according to the invention.

In a further aspect the present invention relates to a curable blend, comprising
(a) one or a plurality of compounds according to the invention or a mixture according to the invention
and
(b) one or a plurality of further constituents selected from the group consisting of
  (b-1) monomers differing from constituent (a), which are copolymerizable with constituent (a), preferably photopolymerizable monomers,
  (b-2) one or a plurality of fillers, preferably one or a plurality of nanoscale fillers,
  (b-3) photoinitiators and initiators for the chemical curing
  (b-4) polymerization inhibitors,
  (b-5) solvents,
  and
  (b-6) adhesion-promoting additives different from constituent (a).

A preferred blend according to the invention relates to a chemically and/or light-induced or heat-induced curing dental composition.

The total amount of the compounds according to the invention of component (a) is preferably in the range 0.1 through 50 wt. %, preferably in the range 5 through 40 wt. %, more preferably in the range 10 through 35 wt. %, in each case in relation to the total weight of the composition.

Constituent (b-1) Polymerizable Monomers

The polymerizable monomers are preferably radically photopolymerizable monomers, preferably substances having one, two or a plurality of ethylenic groups such as for example, but without being limited to, the (meth)acrylate monomers normally used in dental chemistry.

The patent literature mentions a number of other compounds (for example also in DE 3941629 A1, which by way of reference is a constituent of this application), which are all diesters of acrylic or methacrylic acid and are suitable for use in a curable blend according to the invention.

In a preferred curable blend according to the invention constituent (b-1) contains one or a plurality of dimethacrylate monomers selected from the group consisting of ethylene glycol dimethacrylate, 1,6-hexandiol dimethacrylate (HEDMA), triethylene glycol dimethacrylate (TEDMA), 1,12-dodecandiol dimethacrylate, ethoxylated bisphenol A dimethacrylate, polyethylene glycol dimethacrylate, 7,7,9-trimethyl-4,13-dioxo-5,12-diazahexadecan-1,16-dioxy-dimethacrylate (UDMA), butanediol dimethacrylate, tetraethylene glycol dimethacrylate, neopentyl glycol dimethacrylate, 2-hydroxypropyl-1,3-dimethacrylate, 3-hydroxypropyl-1,2-dimethacrylate, pentaerythritol dimethacrylate, glycerin dimethacrylate, bisphenol A glycidyl methacrylate (bis-GMA) and dimethacrylates of dihydroxymethyltricyclo[5.2.1.0$^{2,6}$]decane.

The radical photopolymerizable monomers can also be hydroxyl compounds with at least one ethylenic double bond. Here preferably the hydroxyl compounds of acrylates and methacrylates normally used in dental chemistry can be used. Preferred are hydroxyl compounds of methacrylates, and here in turn preferred are 2-hydroxyethyl methacrylate, 2-hydroxypropyl methacrylate, 3-hydroxypropyl methacrylate, 1,2-dihydroxypropyl methacrylate, 1,3-dihydroxypropyl methacrylate, 2,3-dihydroxypropyl methacrylate, 2-hydroxypropyl-1,3-dimethacrylate, 3-hydroxypropyl-1,2-dimethacrylate, pentaerythritol-dimethacrylate, glycerin dimethacrylate, and 2,2-bis[4-[3-methacryloyloxy-2-hydroxy-propoxy]phenyl]propane.

Photocurable monomers with ethylenic double bonds based on polysiloxanes as for example described in DE 199 03 177 or in DE 44 16 857, which by way of reference are a constituent of this application, can also be used.

A blend preferred according to the invention is characterized in that constituent (b-1) comprises or consists of
(b-1a) one or a plurality of (meth)acrylate monomers, preferably selected from the group consisting of 2-hydroxyethyl methacrylate (HEMA), bisphenol-A-glycidyl-methacrylate (Bis-GMA), 7,7,9-trimethyl-4,13-dioxo-5,12-diazahexadecane-1,16-dioxy dimethacrylate (UDMA), triethylene glycol dimethacrylate (TEDMA), tetraethylene glycol dimethacrylate, polyethylene glycol dimethacrylate, trimethylolpropane trimethacrylate (TMPTMA), dodecanediol dimethacrylate (DODMA), glycerin di(meth)acrylate, 1,6-hexane diol dimethacrylate (HEDMA), ethoxylated bisphenol-A-dimethacrylate, pentaerythritol dimethacrylate, pentaerythritol-tri(meth)acrylate and dipentaerythritolpenta(meth)acrylate,
and/or
(b-1b) one or a plurality of monomers selected from the group consisting of compounds of structure $Q^a(MX_e)_h$, where the following applies:
  $Q^a$ is a polyalicyclic structure element and has, independently of the meaning of the structure element Q in compounds of constituent (a), the meaning given above for Q,
  h is an integer selected from the group of integers 1, 2, 3 and 4,
  each X represents a structure element, which independently of any further structure elements X is selected from the group consisting of

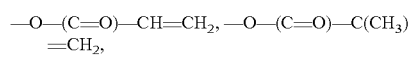

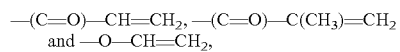

each index e is an integer, which independently of any further indices e is selected from the group of integers 1, 2, 3 and 4,
  each M represents a structure element which, independently of any further structure elements M, in the structure $Q^a(MX_e)_h$ binds the polyalicyclic structure element $Q^a$ with e structure elements X.

The total amount of the monomers of component (b-1) is preferably in the range 0.1 through 60 wt. %, preferably in the range 10 through 50 wt. %, more preferably in the range 15 through 40 wt. %, in each case in relation to the total weight of the blend.

Preferably a blend according to the invention contains two or a plurality of monomers of component (b-1), wherein preferably at least one monomer of component (b-1b) is contained.

Preferred blends according to the invention are characterized in that component (b-1a) contains one or a plurality of (meth)acrylate monomers selected from the group consisting of 2-hydroxyethyl methacrylate (HEMA), bisphenol-A-glycidyl-methacrylate (Bis-GMA), 7,7,9-trimethyl-4,13-dioxo-5,12-diazahexadecane-1,16-dioxy dimethacrylate (UDMA), triethylene glycol dimethacrylate (TEDMA), tetraethylene glycol dimethacrylate, trimethylolpropane trimethacrylate (TMPTMA), glycerin di(meth)acrylate, 1,6-hexane diol dimethacrylate (HEDMA), ethoxylated bisphenol-A-dimethacrylate and dipentaerythritol-penta(meth)acrylate, and mixtures of these.

Preferred blends according to the invention are characterized in that component (b-1b) contains one or a plurality of (meth)acrylate monomers of structure $Q^a(MX_e)_h$, since the monomers of component (b-1b) in combination with the monomer according to the invention of component (a) bring about a further improvement in the characteristics, inter alia a further improved adhesion.

It has also been found that monomers of the above structure $Q^a(MX_e)_h$, preferably (meth)acrylate monomers of structure $Q^a(MX_e)_h$, increase the adhesion of adhesive monomers, particularly the adhesive monomers identified as preferred in the context of the present text.

Therefore the present invention relates to in a further aspect the use of (meth)acrylate monomers of the above structure $Q^a(MX_e)_h$ to increase the bonding characteristics, i.e. to increase the coefficient of adhesion, of adhesive monomers.

This applies in particular also for bis(methacryloyloxymethyl)tricyclo[$5.2.1.0^{2,6}$]decane and/or bis(acryloyloxymethyl)tricyclo[$5.2.1.0^{2,6}$]decane.

A blend preferred according to the invention is thus characterized in that component (b-1b) comprises or consists of bis(methacrylolyoxymethyl)tricyclo[$5.2.1.0^{2,6}$]decane and/or bis(acrylolyoxymethyl)tricyclo[$5.2.1.0^{2,6}$]decane.

Likewise preferred monomers of structure $Q^a(MX_e)_h$ of component (b-1b) are described in DE 10 2010 041 792.0.

The preferred monomers of structure $Q^a(MX_e)_h$ are those wherein the structure element $Q^a$ represents a tricyclo[$5.2.1.0^{2,6}$]decane radical, a tricyclo[$3.3.1.1^{3,7}$]decane radical or a bicyclo[2.2.1]heptane radical.

Preferred monomers of structure $Q^a(MX_e)_h$ are those with one, two, three, four or a plurality of functional groups that are selected from the group consisting of N-acyl urea, allophanate, biuret, and (meth)acrylamide.

Further preferred are monomers of $Q^a(MX_e)_h$, in which h represents 2 or 3.

Preferred are monomers of structure $Q^a(MX_e)_h$ of component (b-1b) in which (i) the structure element X represents —O—(C=O)—C(CH$_3$)=CH$_2$, wherein the functional groups are allophanate, biuret or acyl urea groups, since particularly good results have been obtained with these compounds, and/or (ii) the structure element $Q^a$ represents a tricyclo[$5.2.1.0^{2,6}$] decane radical.

Further preferred are compounds according to the invention, in which the structure element X represents —O—(C=O)—C(CH$_3$)=CH$_2$, wherein the functional groups are allophanate, biuret or acyl urea groups and the structure element $Q^a$ represents a tricyclo[$5.2.1.0^{2,6}$]decane radical.

Constituent (b-2) Fillers

As constituent (b-2) organic and/or inorganic fillers can be used.

Where a blend according to the invention contains one or a plurality of fillers of component (b-2), the total amount of the fillers is preferably in the range 0.5 through 75 wt. %, preferably in the range 10 through 70 wt. %, more preferably in the range 30 through 65 wt. %, in each case in relation to the total weight of the blend.

Inorganic fillers can be used alone or in mixtures. In order to optimize the product features the inorganic fillers can be introduced into the formulations in varying grain sizes. The fillers can have a unimodal or polymodal, for example a bimodal distribution.

The average particle size $d_{50}$ of the filler particles to be used according to the invention of the filler component (b-2) of a blend according to the invention is determined by means of light scattering (laser diffraction), preferably with a Beckman Coulter LS 13320 particle size analyzer.

The fillers of component (b-2) are selected according to the intended purposes of the respective dental material according to the invention, containing the compounds according to the invention.

Thus fillers in blends according to the invention, for example for dental cements such as fixing cements, preferably in the form of microparticles with an average particle size of 0.4 μm through 10 μm are used.

In connection with the present invention, microparticles mean particles with an average particle size of 400 nm through 10 μm. Preferably, the average particle size is less than 5 μm.

The microparticles of component (b-2) can have a monomodal or polymodal, for example a bimodal, particle size distribution. Microparticles with a bimodal or multimodal particle size distribution are preferred according to the invention, since with these a more complete volumetric filling can be achieved than with the general use of microparticles with monomodal particle size distribution. In the case of a bi- or multimodal particle size distribution the particles from the fractions with the larger particle sizes bring about a coarse filling of the volume, while the particles from the fraction with the smaller particle sizes where possible fill the cavities between the particles from the fractions with the larger particle sizes.

Preferably, therefore, in a blend according to the invention, for example in a dental cement, a component (b-2) will be used which contains two or a plurality of fractions of microparticles, wherein the average particle sizes of the fractions differ from one another.

Preferably component (b-2) contains at least two microparticle fractions, wherein the average particle sizes of these differ from one another by at least 0.5 μm, preferably by at least 0.7 μm.

The microparticles of various fractions can comprise the same or different materials; here a plurality of fractions of microparticles can be present, the average particle sizes of which are approximately the same or are within a certain range, wherein the particle materials differ between the fractions.

A blend according to the invention, for example a dental cement, preferably comprises a component (b-2), having one or a plurality of first microparticle fractions, which in each case have an average particle size in the range 1 μm through 10 μm, preferably 1 μm through 5 μm, and one or a plurality of second microparticle fractions, which in each case have an average particle size in the range >0.4 μm through <1 μm (e.g. larger than 0.4 μm, but smaller than 1 μm), preferably in the range 0.5 μm through 0.8 μm.

The ratio of the total weight of the first microparticle fractions to the total weight of the second microparticle fractions is preferably in the range 5:1 through 1:2, preferably in the range 4:1 through 2:3, more preferably in the range 3:1 through 1:1.

The ratio of the average grain size of the or a first microparticle fraction to the average grain size of the or a second microparticle fraction of component (b-2) is preferably in the range 1.5:1 through 12:1, preferably in the range 2:1 through 7:1.

In a particularly preferred blend according to the invention, for example in a dental cement, the component (b-2) comprises one or a plurality of first microparticle fractions, which in each case have an average particle size in the range 1 μm through 10 preferably 1 μm through 5 and one or a plurality of second microparticle fractions, which in each case have an average particle size in the range >0.4 μm through <1 preferably 0.5 μm through 0.8 wherein the ratio of the total weight of the first microparticle fractions to the total weight of the second microparticle fractions is in the range 5:1 through 1:2, preferably in the range 4:1 through 2:3 and/or the ratio of the average grain size of the or a first microparticle fraction to the average grain size of the or a second microparticle fraction of component (b-2) is in the range 1.5:1 through 12:1, preferably 2:1 through 7:1.

For better bonding in the polymer matrix of a composition according to the invention the microparticles can be organically surface-modified. One example of surface treatment of the fillers is the use of a silane, leading to silanized microparticles. Methacryloxypropyltrimethoxysilane is particularly well-suited for surface treatment (as a bonding agent).

A blend containing a microparticle according to the invention, for example a dental cement, can also contain nanoscale fillers.

Compact glasses and various silicic acids in different sizes and states (monodisperse, polydisperse) are used, for example, as inorganic fillers.

Suitable inorganic components are for example amorphous materials with a mixed oxide base of $SiO_2$, $ZrO_2$ and/or $TiO_2$, microfine fillers such as pyrogenic silicic acid or precipitated silicic acid and macro- or mini-fillers such as quartz-glass ceramic or glass powder, barium silicate glasses, barium fluorosilicate glasses, strontium silicate glasses, strontium borosilicate, Li/Al silicate glasses, barium glasses, calcium silicates, sodium aluminum silicates, fluoroaluminum silicate glasses, oxides of aluminum or silicon, zeolites, apatite, zircon mineral, hardly soluble metal salts such as barium sulfate or calcium fluoride and X-ray opaque fillers such as ytterbium fluoride.

Preferred radiopaque fillers are selected from the group consisting of zinc, ytterbium, yttrium, zirconium, strontium, calcium, titanium, tungsten, tantalum, niobium, barium, bismuth, molybdenum in the form of alloys, oxides, fluorides, oxohalogenides, sulfates, phosphates, silicates, carbonates, tungstates or glasses and mixtures of these.

Advantageous radiopaque fillers here are $CaWO_4$, $ZrO_2$, ytterbium fluoride, barium sulfate and/or radiopaque glasses.

In order to adjust the rheology curable blends and products according to the invention can contain various silicic acids, preferably pyrogenic silicic acids.

In addition materials with a strengthening effect such as glass fibers, polyamide or carbon fibers can be used. The curable blends and products according to the invention can also contain fine particle splinters or bead polymers, wherein the bead polymers can be homo- or copolymers or organically curable monomers. The organic fillers can basically be used in differing grain sizes, such as for example ground polymers and prepolymers.

Likewise the curable blends and products according to the invention, particularly for use in dentistry, for example in blends and products for coating tooth surfaces, preferably contain nanoscale solid particles. Nanoscale solid particles are particles with an average particle size of not more than 200 nm, preferably not more than 100 nm and preferably not more than 70 nm. The nanoscale inorganic solid particles are preferably those of metal oxides, phosphates, sulfides, selenides and tellurides and mixtures of these. Particularly preferred are nanoscale particles of $SiO_2$, $TiO_2$, $ZrO_2$, $ZnO$, $SnO_2$ and $Al_2O_3$ and mixtures of these. The preparation of nanoscale solid particles takes place in ways that are known, e.g. by flame pyrolysis, the plasma method, gas-phase condensation, colloidal techniques, precipitation methods, sol-gel method, etc.

In order to allow the nanoparticles to achieve a proper bonding in the polymer matrix of a curable blend or product according to the invention, the surfaces of the nanoparticles (preferably the preferred oxidic nanoparticles) are organically modified, i.e. their surfaces have organic structure elements. One example of surface treatment of the fillers is the use of a silane, leading to the formation of silanized nanoparticles. Methacryloxypropyltrimethoxysilane is particularly well-suited as a bonding agent here.

In a further preferred configuration the nanoscale particles are non-agglomerated, organically surface-modified nanoparticles with an average particle size of less than 200 nm, preferably less than 100 nm, particularly preferably less than 70 nm, preferably in the range 5 through 60 nm, for example dispersed in a medium, in particular in monodisperse form, wherein these nanoparticles are in turn preferably silanized.

Constituent (b-3)—Photoinitiators

Examples of a photoinitiator include catalysts which have solely a photo-sensitizing effect and combinations of sensitizers and accelerators.

Examples of photosensitizers are alpha-diketones, benzoin alkyl ethers, thioxanthones, benzophenones, phosphonic oxides, acylphosphine oxides, aryl iodonium salts, acetophenones, ketals, titanocenes, sensitizing colorants, etc. The sensitizers can be used alone or in combination. Specific substance examples of the various classes can be found, for example, in DE 10 2006 019092 A1 or in DE 3941629 C2, which by way of reference are a constituent of this application.

Examples of accelerators, which are used together with the sensitizers, are tertiary amines, secondary amines, barbituric acids, tin compounds, aldehydes and sulfur compounds. Specific substance examples of the various classes can be found in DE 10 2006 019092 A1 or in DE 3941629 C2, which by way of reference are a constituent of this application.

Further suitable initiators and initiator combinations are described in DE 60116142, which by way of reference are a constituent of this application.

The photoinitiators used in connection with the present invention are characterized in that through the absorption of light in the wavelength range 300 nm through 700 nm, preferably 350 nm through 600 nm and particularly preferably 380 through 500 nm, optionally in combination with one or a plurality of co-initiators, they can bring about the curing of a mixture that is curable according to the invention.

The absorption maximum of campherquinone (CQ) is approximately 470 nm and thus in the range of blue light. Campherquinone (CQ) is one of the $PI_2$-initiators and is regularly used together with a co-initiator.

A curable blend according to the invention preferably contains the combination of an alpha-diketone and an aromatic tertiary amine, preferably the combination is of campherquinone (CQ) and ethyl-p-N,N-dimethylaminobenzoate (DABE)

Likewise preferred is the further combination of the "alpha-diketone/aromatic tertiary amine" system with a phosphine oxide, preferably with phenyl-bis(2,4,6-trimethylbenzoyl)phosphine oxide and/or 2,4,6-trimethylbenzoyldiphenyl phosphine oxide. Regarding the structures of suitable phosphine oxides for use in mixtures that can be cured according to the invention reference is made to printed publications DE 3801511 C2, DE 10 2006 050153 A1, EP 0184095 B1, DE 4231579 C2, EP 0366977 B1, U.S. Pat. No. 7,081,485 B2, DE 3236026 A1, US 2007/0027229 A1, EP 0262629 B1, EP 0073413, U.S. Pat. No. 7,148,382 B2, U.S. Pat. No. 5,761,169, DE 19708294 A1, EP 0057474, EP 0047902 A, EP 0007508, DE 60029481 T2, EP 0980682 B1, EP 0948955 B1, EP 1236459 B1 and EP 0 173567 A2, which by way of reference are a constituent of this application.

The phosphine oxides indicated in these printed publications are particularly suitable on their own or in combination with the "alpha-diketone/amine" system as a photopolymerization initiator system in the mixtures according to the invention.

Alternatively borate salts, as described for example in U.S. Pat. No. 4,772,530, U.S. Pat. No. 4,954,414, U.S. Pat. No. 4,874,450, U.S. Pat. No. 5,055,372 and U.S. Pat. No. 5,057,393, can be used as photoinitiators, which by way of reference are a constituent of this application.

Further suitable photoinitiators are described in J.-P. Fouassier, Photoinitiation, Photopolymerization and Photocuring, Hanser Publishers, Munich, Vienna, New York 1995 and in J. F. Rabek (publisher), Radiation Curing in Polymer Science and Technology, Vol. II, Elsevier Applied Science, London, New York 1993, which by way of reference are a constituent of this application.

Constituent (b-3)—Initiators for the Chemical Curing

Various initiators for a chemical curing will be known to a person skilled in the art. In this connection reference is made by way of example to EP 1720506.

Suitable initiators for the chemical radical curing include peroxides and amines or sulfinic acid/acid salts such as for example dibenzoylperoxide (BPO) in combination with N,N-bis-(hydroxyethyl)-para-toluidine (N,N-Bis) or sodium sulfinate as well as barbituric acid derivatives such as benzyl phenyl barbituric acid and soluble copper and tetraalkylammonium chloride salts, trialkylborane and azo bis iso butyro nitril (AlBN).

Preferred initiators for chemical curing are benzoyl peroxide, lauroyl peroxide preferably dibenzoyl peroxide in combination with amines such as N,N-dimethyl-p-toluidine, N,N-dihydroxyethyl-p-toluidine and structurally related amines.

Here the peroxides and the amines are spread across two different components of the dental material. During the mixing of the amine-containing components (so-called base paste) with the peroxide-containing components (so-called initiator or catalyst paste) through the reaction of amine and peroxide (redox reaction) the radical reaction is initiated.

Dual-curing systems comprise a combination of photoinitiators and initiators for chemical curing.

By way of example, the base paste can also contain a photoinitiator, so that the base paste can be used either on its own as a photo-curing agent or together with the initiator paste as a photo- and self-curing dental material.

Apart from the organic peroxide compounds with an oxidative effect, barbituric acids or barbituric acid derivatives and malonyl sulfamides can also be used as redox systems.

Of the barbituric acid systems the so-called Bredereck systems are of great significance. Examples of suitable Bredereck systems and references to the corresponding patent literature can be found in EP 1839640 and in DE 1495520, WO 02/092021 or in WO 02/092023, which by way of reference are a constituent of this application.

Suitable malonyl sulfamides are described in EP 0059451 which by way of reference is a constituent of this application. Preferred compounds here are 2,6-dimethyl-4-isobutylmalonyl sulfamide, 2,6-diisobutyl-4-propylmalonyl sulfamide, 2,6-dibutyl-4-propylmalonyl sulfamide, 2,6-dimethyl-4-ethylmalonyl sulfamide and 2,6,6-diocytyl-4-isobutylmalonyl sulfamide.

Sulfur compounds in the oxidation stage+2 or +4 such as sodium benzene sulfinate or sodium paratoluene sulfinate can also be used.

In order to accelerate the curing the polymerization can be carried out in the presence of compounds of heavy metals such as Ce, Fe, Cu, Mn, Co, Sn or Zn, wherein copper compounds are particularly preferred. The heavy metal compounds are preferably used in the form of soluble organic compounds. Preferred copper compounds here are copper benzoate, copper acetate, copper ethyl hexanoate, copper di(methacrylate) and copper napththenate.

Constituent (b-4)—Polymerization Inhibitors

The curable blends according to the invention preferably contain one or a plurality of inhibitors, also referred to as stabilizers. These are added to a curable blend in order to prevent spontaneous polymerization. They react with prematurely forming radicals, which are intercepted, prevent premature polymerization and increase the storage stability of the curable, preferably photocurable, preferably dental, blend.

Common inhibitors are phenol derivates such as hydroquinone monomethylether (HQME) or 2,6-di-tert.butyl-4-methylphenol (BHT). Further inhibitors such as 2,2diphenyl-1-picrylhydrazyl, galvinoxyl, triphenylmethyl radicals, 2,3,6,6,-tetramethylpiperidinyl-1-oxyl radicals (TEMPO) and derivatives of TEMPO or phenothiazine and derivatives of this compound are described in EP 0 783 880 B1 which by way of reference are a constituent of this application. Alternative inhibitors are indicated in DE 10119831 A1 or in EP 1563821 A1, which by way of reference are a constituent of this application.

These stabilizers can also be used to regulate the redox initiation.

Constituent (b-5)—Solvents

A blend according to the invention preferably contains one or a plurality of solvents, preferably in a total quantity of 5 through 65 wt. %, preferably in a total quantity of 10 through 50 wt. %, in each case in relation to the total weight of the blend.

A blend according to the invention can contain water as a solvent.

Also suitable are the inorganic solvents commonly used, such as for example hydrocarbons, ketones and esters such as for example toluene, xylene, isooctane, acetone, butanone, methyl isobutyl ketone, ethyl acetate, butyl acetate, tetrahydrofuran, N-methylpyrrolidone, dimethyl acetamide and dimethyl formamide. Alcohols can also be used such as ethanol, propanols, butanols, pentanols, hexanols, cyclohexanol, heptanols, octanols, nonanols, decanols, etc. Similarly suitable are cycloaliphatic or arylaliphatic alcohols.

In a preferred configuration a blend according to the invention contains an organic solvent, preferably selected from the group consisting of organic solvents miscible with water, preferably acetone, ethanol, n-propanol and isopropanol and mixtures of these.

Particularly preferably a blend according to the invention contains water and at least one organic solvent miscible with water, here preferably acetone. Here the ratio of acetone to water is preferably in the range 1:1 through 10:1, preferably in the range 2:1 through 8:1, more preferably in the range 3:1 through 5:1.

Constituent (b-6)—Adhesion-Promoting Additives

In order to achieve even better adhesion to the tooth enamel and/or dentin, the compounds according to the invention can preferably be combined with one or a plurality of further adhesion-promoting additives.

Preferred are therefore blends according to the invention, which contain as component (b-6) one or a plurality of further adhesion-promoting additives. Here also the configurations identified as preferred or particularly preferred apply by analogy.

Further preferred are blends according to the invention comprising
(a) one or a plurality of compounds according to the invention or a mixture according to the invention, preferably in one of the configurations identified as preferred or particularly preferred, and
(b-6) one or a plurality of adhesion-promoting additives, selected from the group consisting of polymerizable or non-polymerizable acids or carboxylic acid anhydrides, preferably from the group consisting of phosphoric acids, phosphonic acids, carboxylic acids and their salts, carboxylic acid esters and carboxylic acid anhydrides, preferably in a quantity in the range 0.1 through 35 wt. %, more preferably in a quantity in the range 0.25 through 25 wt. %, particularly preferably in a quantity in the range 0.5 through 15 wt. %, in each case in relation to the total weight of the blend.

Preferably the one or a plurality of further adhesion-promoting additives of component (b-6) is/are selected from the group consisting of
10-(meth)acryloyloxydecyl dihydrogen phosphate (10-MDP), 2-(meth)acryloyloxyethyl dihydrogen phosphate, 6-(meth)acryloyloxyhexyl dihydrogen phosphate, 4-(meth)acryloyloxybutyl dihydrogen phosphate, 8-(meth)acryloyloxyoctyl dihydrogen phosphate, 2-(meth)acryloyloxynonyl dihydrogen phosphate, 11-(meth)acryloyloxyundecyl dihydrogen phosphate, 20-(meth)acryloyloxyeicosyl dihydrogen phosphate, 1,3-di(meth)acyloyloxypropyl-2-dihydrogen phosphate, 2-(meth)acryloyloxyethylphenyl dihydrogen phosphate, di(2-(meth)acyloyloxyethyl)pyrophosphate, di(2-(meth)acyloyloxypropyl)pyrophosphate, di(2-(meth)acyloyloxybutyl)pyrophosphate, di(2-(meth)acyloyloxypentyl)pyrophosphate, the di(2-(meth)acyloyloxyhexyl)pyrophosphate, di(2-(meth)acyloyloxydecyl)pyrophosphate, mono-, di- and/or triesters of phosphoric acid, obtained by reaction of hydroxy-C2-C8-alkyl methacrylate (here preferably hydroxyethyl methacrylate) or glyceryl dimethacrylate with phosphoroxy chloride, glyceryl dimethacrylate phosphate, pentaerythritol trimethacrylate phosphate, dipentaerythritol-pentaacrylate phosphate, tetramethacryloxyethyl pyrophosphate, 4-(methacryloyloxyethyl) trimellitic acid, trimellitic acid-4-methacryloyloxy ethyl ester (4-MET), trimellitic acid anhydride-4-methacryloyloxy ethyl ester (4-META), pyromellitic acid dimethacrylate, pyromellitic acid glycerol dimethacrylate, methacryloyloxy ethyl phthalate, methacryloyloxy ethyl maleate, methacryloyloxy ethyl succinate, 1,3-glycerol dimethacrylate maleate and di-oxyethoxy methacrylic acid ethylene diamine tetraacetic acid ester.

Here in turn preferred further adhesion-promoting additives of component (b-6) are 10-(meth)acryloyloxydecyl dihydrogen phosphate (10-MDP), glyceryl dimethacrylate phosphate, pentaerythritol trimethacrylate phosphate, dipentaerythritol pentaacrylate phosphate, tetramethacryloxy ethyl pyrophosphate, trimellitic acid-4-methacryloyloxy ethyl ester (4-MET), trimellitic acid anhydride-4-methacryloyloxy ethyl ester (4-META), pyromellitic acid dimethacrylate, pyromellitic acid glycerol dimethacrylate.

In the following the invention is explained in more detail for monomers comprising tricyclic structure elements Q using the example of tricyclo[$5.2.1.0^{2,6}$]decane (TCD)-derivatives.
1.) Starting with the bis(hydroxymethyl)tricyclo[$5.2.1.0^{2,6}$]decane (TCD-diol)
bis(hydroxymethyl)tricyclo[$5.2.1.0^{2,6}$]decane is commercially available, for example as a dicidol mixture of the isomeric compounds 3,8-bis(hydroxymethyl)tricyclo[5.2.1. $0^{2,6}$]decane and 4,8-bis(hydroxymethyl)tricyclo[$5.2.1.0^{2,6}$]decane as well as 3,9-bis(hydroxymethyl)tricyclo[$5.2.1.0^{2,6}$]decane and 4,9-bis(hydroxymethyl)tricyclo[$5.2.1.0^{2,6}$]decane.

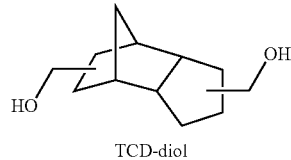

TCD-diol

The bis(hydroxymethyl)tricyclo[$5.2.1.0^{2,6}$]decanes can, starting with dicyclopentadiene (tricyclo[$5.2.1.0^{2,6}$]deca-3,8-diene), be synthesized. Dicyclopentadiene is easily accessible in a Diels-Alder reaction by dimerization of cyclopentadiene. Hydroformylation of dicyclopentadiene then produces the bis(hydroxymethyl)tricyclo[$5.2.1.0^{2,6}$]decane. According to the synthesis route taken bis(hydroxymethyl)tricyclo[$5.2.1.0^{2,6}$]decanes specifically substituted at different positions can be obtained. Thus in published documents JP 7-206740, EP 1112995 B1 or EP 0049631 B1 specifications are provided on how, for example, the 8,9-bis(hydroxymethyl)tricyclo[$5.2.1.0^{2,6}$]decane is preparable. DE 10352260 B3 on the other hand describes a method for preparing 3(4), 8(9)-bis(hydroxymethyl)tricyclo[$5.2.1.0^{2,6}$]decane. The notation of the positions of the hydroxymethyl groups 3(4), 8(9) means 3 or 4, 8 or 9.

The reaction of the 3(4), 8(9)-bis(hydroxymethyl)tricyclo[$5.2.1.0^{2,6}$]decanes with isocyanates to form the corresponding urethanes is likewise known. Thus DE 3522006 A1 describes the reaction of the 3(4), 8(9)-bis(hydroxymethyl)tricyclo[$5.2.1.0^{2,6}$]decane with 2-isocyanatoethyl methacrylate. 2-isocyanatoethyl methacrylate is commercially available or can be synthesized according to the preparation specification from DE 3338077 A1 by phosgenation of dihydrooxazines.

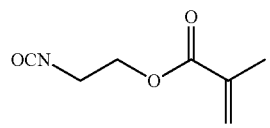

2-isocyanatoethyl methacrylate

The reaction of 3(4), 8(9)-bis(hydroxymethyl)tricyclo[$5.2.1.0^{2,6}$]decane with 2-isocyanatoethyl methacrylate results in a compound of Formula (1):

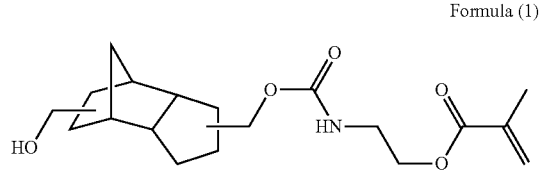

Formula (1)

The reaction of 3(4), 8(9)-bis(hydroxymethyl)tricyclo[$5.2.1.0^{2,6}$]decane with methacryloyl isocyanate results in a compound of Formula (2):

Formula (2)

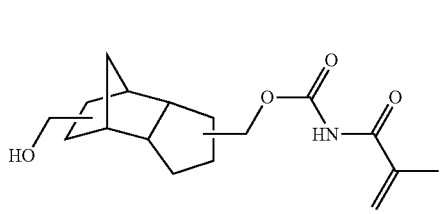

The respective reaction of the compound of Formula (1) or the Compound of Formula (2) with POCl₃ following hydrolysis results in the compound of Formula (3) or of Formula (4) according to the invention.

Formula (3)

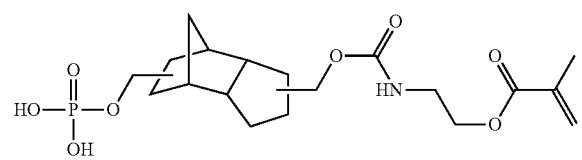

Formula (4)

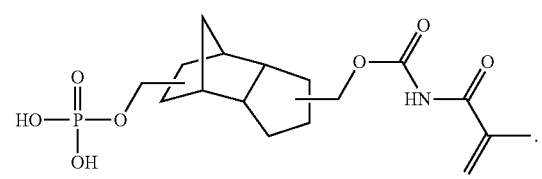

The reaction of the compound of Formula (1) with ethylene glycol results in the compound of Formula (5), the subsequent reaction with POCl₃ of which, following hydrolysis, results in the compound of Formula (6) according to the invention.

Formula (5)

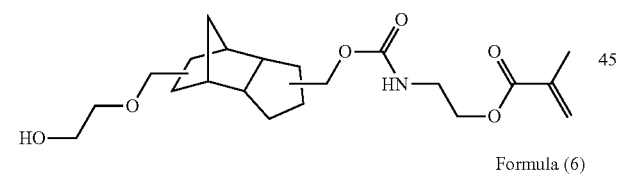

Formula (6)

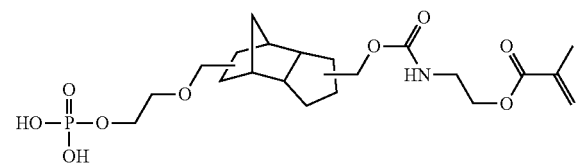

Corresponding reactions for the purposes of comparison:

Starting with TCD-diol, for the purposes of comparison, through reaction with methacrylic acid chloride the compound of Formula (7) not according to the invention was obtained, for the synthesis see also Example 3. The further reaction of compound (7) with POCl₃ and subsequent hydrolysis resulted in the compound of Formula (8) not according to the invention, for the synthesis see also Example 4.

Formula (7)

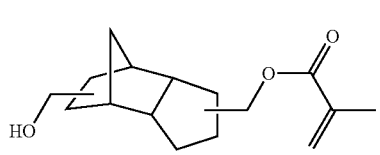

Formula (8)

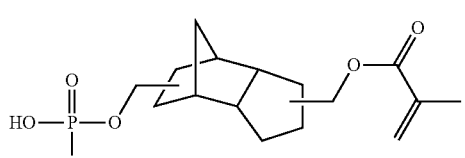

2.) Starting with 3(4), 8(9)-bis(aminomethyl)tricyclo [5.2.1.0$^{2,6}$]decane

The 3(4), 8(9)-bis(aminomethyl)tricyclo[5.2.1.0$^{2,6}$]decane is in itself known and is preparable for example by reaction of the corresponding tosylates with ammonia.

Reaction of the 3(4), 8(9)-bis(aminomethyl)tricyclo [5.2.1.0$^{2,6}$]decane with 2-isocyanatoethyl methacrylate results in the urea compound of Formula (9), which in a sense is an intermediate products of the diurea compound described in EP 0209700 A2.

Formula (9)

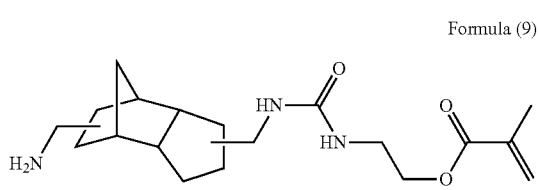

The reaction of 3(4), 8(9)-bis(aminomethyl)tricyclo [5.2.1.0$^{2,6}$]decane with methacryloyl isocyanate results in a compound of Formula (10):

Formula (10)

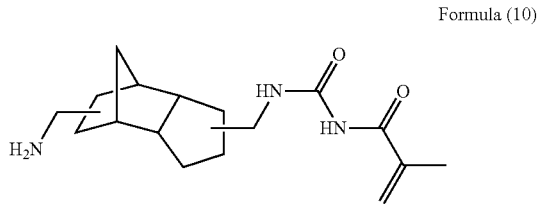

The respective reaction of the compound of Formula (9) or the Compound of Formula (10) with POCl₃ following hydrolysis results in the compound of Formula (11) or of Formula (12) according to the invention.

Formula (11)

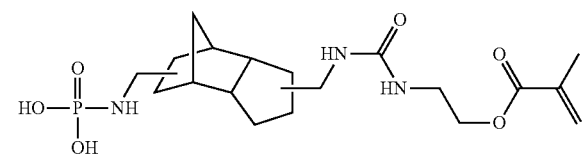

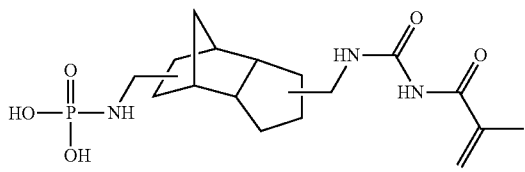
Formula (12)

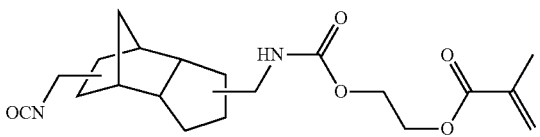
Formula (15)

The reaction of the compound of Formula (9) with ethylene glycol results in the compound of Formula (13), the subsequent reaction with $POCl_3$ of which, following hydrolysis, results in the compound of Formula (14) according to the invention.

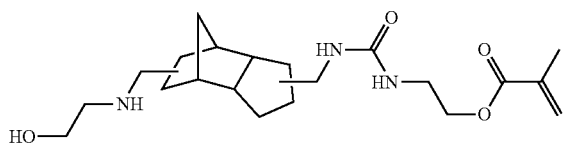
Formula (13)

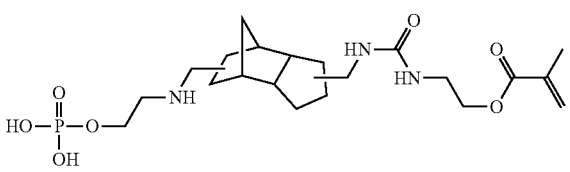
Formula (14)

3.) Starting with 3(4), 8(9)-bis(isocyanatomethyl)tricyclo$[5.2.1.0^{2,6}]$decane The 3(4), 8(9)-bis(isocyanatomethyl)tricyclo$[5.2.1.0^{2,6}]$ decane is in itself known and is one of the diisocyanate compounds commonly used in industrial applications (see DE 3703120 A1 and WO 2009/065873 A2).

Reaction of the 3(4), 8(9)-bis(isocyantomethyl)tricyclo $[5.2.1.0^{2,6}]$decane with 2-hydroxyethyl methacrylate (HEMA) results in the urethane of Formula (15):

Instead of 2-hydroxyethyl methacrylate (HEMA) in these reactions described by way of example other hydroxyl compounds of (meth)acrylates can be used, wherein blends of acrylates and methacrylates can also be used. Also preferred are hydroxypropyl(meth)acrylate, 2-hydroxypropyl(meth)acrylate, hydroxybutyl(meth)acrylate, 4-hydroxybutyl(meth)acrylate, hydroxypentyl(meth)acrylate, 3-hydroxy-2,2-dimethylpropyl(meth)acrylate, hydroxyhexyl(meth)acrylate, hydroxyheptyl(meth)acrylate, hydroxyoctyl(meth)acrylate, hydroxynonyl(meth)acrylate, hydroxydecyl(meth)acrylate, hydroxyundecyl(meth)acrylate and hydroxydodecyl(meth)acrylate, wherein in this connection 2-hydroxyethyl methacrylate(HEMA) is most preferred.

Reaction of the 3(4), 8(9)-bis(isocyantomethyl)tricyclo $[5.2.1.0^{2,6}]$decane with 2-methacrylic acid under decarboxylation results in the methacrylamide of Formula (16):

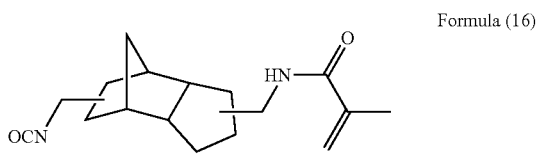
Formula (16)

The reaction of the compound of Formula (15) or (16) with ethanol amine (corresponding to 2-aminoethanol) results in the compounds not according to the invention of Formula (17) and (18); the subsequent reaction in each case with $POCl_3$ following hydrolysis results in the compounds according to the invention of Formula (19) and Formula (20) respectively.

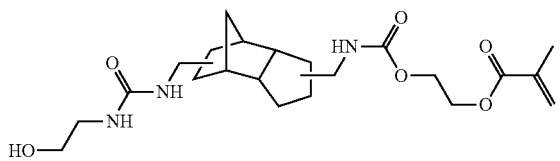
Formula (17)

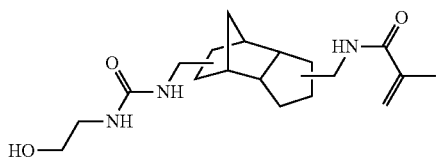
Formula (18)

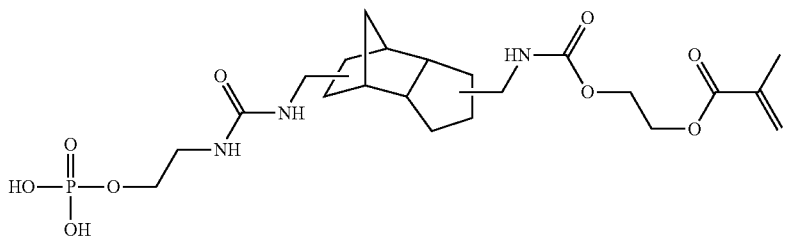
Formula (19)

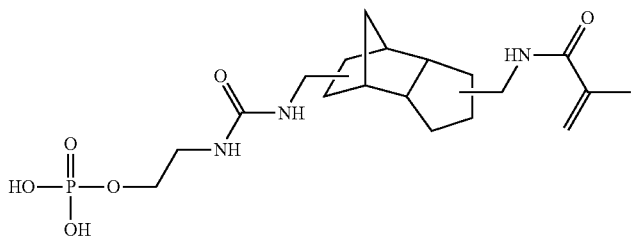

Formula (20)

The preparation of compounds of formula HG-(L)$_x$-Q(YZ)$_b$ is in general carried out in an inert solvent such as THF (tetrahydrofuran), toluene, xylene, methylene chloride or acetonitrile. The reaction can also be conducted optionally without a solvent.

There are two main classes of suitable catalysts for the isocyanate addition reaction: firstly tertiary amines (such as tri-N,N-dimethylaminomethyl phenol or 1,4-diazabicyclo(2,2,2)octane, also referred to as triethylene diamine), which through abstraction of the hydroxyl hydrogen atom and formation of alcoholate anions activate the alcohols and thus accelerate their nucleophilic attack on the isocyanate carbon atom, and secondly a series of metalorganic compounds, which as Lewis acids increase the electrophilia of the isocyanate hydrogen atom. Preferably used for the reactions according to the invention are metal salts of higher fatty acids such as dibutyltin laurate, tin (II) octoate, etc. or compounds such as iron (III) acetylacetonate. Highly preferred is the use of dibutyltin laurate.

The catalyst is preferably used in quantities of 0.01 through 2 wt. %, preferably 0.08 through 1 wt. %, in relation to the total quantity of reactants.

In a preferred embodiment the method can comprise the addition of a polymerization inhibitor. Common and suitable inhibitors are for example hydroquinone monomethylether, hydroquinone and 2,6-di-tert.-butyl-4-methyl phenol. Further suitable inhibitors are mentioned in EP 0783880. The addition of inhibitors generally takes place in a quantity of 0.001 through 1 wt. %, preferably 0.01 through 0.5 wt. %, in relation to the total weight of the reactants.

The method is preferably performed with the exclusion of water. For the synthesis, preferably a surface-grinding apparatus is then used, to which an agitator, a cooler with drying tube fitted, which is filled with dry kieselgur, an adjustable thermometer that control the heating rate of the mushroom heater, and a dropping funnel are attached. The apparatus is heated with a Bunsen burner flame prior to being loaded with the educts.

The reaction preferably takes place in the temperature range 0 through 160° C., preferably in the range 30 through 140° C. and particularly preferably in the range 60 through 120° C. The reaction is preferably carried out at normal pressure (1013 mbar).

The progress of the reaction is monitored by the change in concentration of isocyanate groups. The reaction of the isocyanate groups can take place according to the wet chemical or spectroscopic routes. The wet chemical principle for analysis of the isocyanate groups is based on the quantitative reaction of the isocyanate with an excess of dibutyl amine and back titration of the excess amine with hydrochloric acid against bromophenol blue until the blue turns to yellow. Spectroscopically, NCO groups absorb in wavelengths of 2275 through 2250 cm$^{-1}$. The band demonstrates a very high intensity in this range, the position of which is also not influenced by conjugation. The characteristic wavelength range of the NCO band is identified if a purely qualitative spectrum of the isocyanate compound in a suitable solvent, which should also be used for the further syntheses, is created. The solvent should not have any absorption bands in the wavelength range, which demonstrate the characteristic absorption bands of the NCO group. If for example toluene is used as the solvent, then the extinction maximum of the NCO band at 2267 cm$^{-1}$ can be selected as a "window", thus as the wavelength range of the characteristic absorption band.

The reaction is conducted until the isocyanate band disappears completely.

The compounds of formula HG-(L)$_x$-Q(YZ)$_b$ can advantageously also be used without any special methods for purification.

In order to prepare the compounds according to the invention the component HG-(L)$_x$-Q(YZ)$_b$ is reacted with POCl$_3$ or phosphorous(V) oxide.

The preparation of the compounds according to the invention is carried out in an inert solvent, preferably in an ether such as THF (tetrahydrofuran), diethyl ether, methyl-tert-butyl ether or 1,4-dioxane. The solvent should be anhydrous.

In a preferred embodiment the method comprises the addition of a polymerization inhibitor. Common and suitable inhibitors are for example hydroquinone monomethylether, hydroquinone and 2,6-di-tert.-butyl-4-methyl phenol. Further suitable inhibitors are mentioned in EP 0783880. The addition of inhibitors generally takes place in a quantity of 0.001 through 1 wt. %, preferably 0.01 through 0.5 wt. %, in relation to the total weight of the reactants.

The method is performed with the exclusion of water. For the synthesis a surface-grinding apparatus is used, to which an agitator, a cooler with drying tube fitted, which is filled with dry kieselgur, an internal thermometer and a dropping funnel are attached. Prior to being filled with the educts the apparatus is heated using a Bunsen burner flame.

In order to increase the reactivity in a first step the component HG-(L)$_x$-Q(YZ)$_b$ can initially be deprotonated by the addition of a basic component, such as for example an alkaline hydroxide, a tertiary organic amine or a tertiary alcoholate. A tertiary amine is preferably used for this, with triethyl amine or pyridine being particularly preferred. The deprotonation is achieved by dissolving the component HG-(L)$_x$-Q(YZ)$_b$ in the inert solvent and subsequent addition of the basic component.

The reaction takes place preferably in a temperature range of −90° C. through 20° C. and preferably in the range −70° through 0° C. The reaction is preferably carried out at normal pressure (1013 mbar).

The reaction preferably lasts for between 0.5 and 24 hours. As a rule it can be over within 0.5 through 3 hours.

The hydrolysis of the intermediate product from reaction step ii) of the preparation method according to the invention takes place by addition of water. In the case of reaction with POCl$_3$, in order to prevent a reversal of the reaction, the hydrogen chloride being released is bonded to a suitable base. A tertiary amine is generally used for this, with triethyl amine or pyridine preferably being used.

The monomers according to the invention can be used individually, as mixtures comprising two or a plurality of monomers according to the invention and in mixtures with one or a plurality of conventional monomers and so-called cross-linkers. By mixing two or a plurality of different monomers according to the invention or one, two or a plurality of monomers according to the invention with one, two or a plurality of conventional monomers the viscosity, for example, can be adapted to the intended purpose. Thus monomers according to the invention can for example be combined with comonomers of lower viscosity.

The monomers according to the invention can be used everywhere, liquid, flowable starting materials are to be cured to form solid end products. The transition from the liquid to the solid phase is initiated here chemically, by radiation or by both (i.e. both chemically and by means of radiation). Curing is by a radical and/or ionic mechanism. Polymerization initiators that can be used are thus photoinitiators and thermal polymerization catalysts. A person skilled in the art will be acquainted with radical photoinitiators, radical thermoinitiators, cationic photoinitiators and cationic thermoinitiators and combinations of these.

Blends according to the invention comprising the monomers according to the invention can contain various additives, activators, coinitiators, solvents, fillers, stabilizers, pigments, reactive thinners, comonomers, inhibitors, molecular weight regulators, flow agents, leveling agents, antiskinning agents, defoamers, antistatics, plasticizers, lubrication agents, wetting agents and dispersing agents, preservatives such as for example fungicides and/or biocides, modifiers to adjust the rheology such as thixotropic agents and/or thickeners, sensitizers, surface-active substances, oxygen and/or radical scavengers, pigments, colorants, light stabilizers, matting agents, fire retardants, release agents, and so on, adapted to the intended use.

UV absorbers, which for example as a result of their conjugated double bonding system and aromatic rings are capable of absorbing UV radiation, can optionally also be a constituent of a blend or product according to the invention. Examples of UV absorbers are 2-hydroxy-4-methoxybenzophenone, salicylic acid phenyl ester or 3-(2'-hydroxy-5'-methylphenyl)-benzotriazole.

A dental blend or product preferred according to the invention further comprises as an additive, one or a plurality of fluoride-releasing substances here preferably sodium fluoride and/or aminofluoride.

Additionally, one or a plurality of surfactants can be a constituents of a blend or product according to the invention.

The invention further relates to a product obtainable by curing a compound according to the invention, a mixture according to the invention or a blend according to the invention.

A product according to the invention preferably relates to a polymer or a composite, preferably a dental polymer or a dental composite material.

The invention further relates to a compound according to the invention, a mixture according to the invention, a blend according to the invention or a product according to the invention as a dental material or for use as a dental material.

The invention further relates to the use of a compound according to the invention, a mixture according to the invention, a blend according to the invention or a product according to the invention for the preparation of a dental material.

For example, the method of using the compound, mixture, blend or product as a dental material can include providing the compound, mixture, blend or product as described herein and applying the compound, mixture, blend or product composition to a surface, such as tissue of a patient. The method can be part a medical procedure, e.g., a dental procedure. The method can include applying the compound, mixture, blend or product composition as a dental material, preferably in or for the preparation of bonding agents, preferably dental bonding agents; in or for the preparation of filling and/or sealing materials, preferably dental filling materials, underfilling materials, fissure sealing materials, root canal filling and/or sealing materials; in or for the preparation of lacquers, preferably gloss lacquers and/or surface lacquers, preferably dental gloss lacquers and/or surface lacquers; in or for the preparation of flowable composite materials (flow materials), preferably dental composites; in or for the preparation of dental temporary restoration materials (preferably temporary inlays, onlays, crowns, bridges, fixing materials) and/or stump build-up materials; and/or in or for the preparation of adhesive, coloring, painting or coating compositions, compounds, sealants, fillers, laminating resins, molding masses, binding agents or casting resins. The method can further include curing the compound, mixture, blend or product. As used herein, "tissue" is intended to have its conventional meaning and include all features of teeth.

The compounds, mixtures and blends according to the invention can be used preferably in or for the preparation of composites and in or for the preparation of dental materials (dental compositions).

The invention further relates to a method for preparing a product, preferably a dental product, with the following steps:
(i) providing a compound according to the invention, a mixture according to the invention or a blend according to the invention, in each case preferably in one of the configurations identified as preferred or particularly preferred, as a first component;
(ii) optionally preparing a preparation through mixing of the first component with one or a plurality of further components, preferably with one or a plurality of further dental materials;
(iii) curing the component(s) from step (i) or the preparation according to step (ii), wherein the curing preferably takes place chemically and/or is light induced or thermally induced.

In a preferred configuration for this purpose the first component or the preparation according to step (ii) before curing in step (ii) is applied to, introduced into and/or placed at the envisaged position, preferably a position in the oral cavity, wherein this position preferably comprises one or a plurality of areas of the oral cavity from the group consisting of tooth structure (one or a plurality of teeth or parts of a tooth (preferably tooth stump, enamel, dentin, pulp, tooth neck, tooth edge)), gum and/or an area below a tooth (preferably root and root canal).

The invention further relates to a compound according to the invention, a mixture according to the invention, a curable blend according to the invention or a product according to the invention, in each case preferably in one of the configurations identified as preferred, in or for the preparation of bonding agents, preferably dental bonding agents, in or for the preparation of filling and/or sealing materials, preferably dental filling materials, underfilling materials, fissure sealing materials, root canal filling and/or sealing materials, in or for the preparation of lacquers, preferably gloss lacquers and/or surface lacquers, preferably dental gloss lacquers and/or surface lacquers, in or for the preparation of flowable composite materials (flow materials), preferably dental composites, in or for the preparation of dental temporary restoration materials (preferably temporary inlays, onlays, crowns, bridges, fixing materials) and/or stump build-up materials, in or for the preparation of adhesive, coloring, painting or coating compositions, compounds, sealants, fillers, laminating resins, molding masses, binding agents or casting resins.

The invention further relates to a method for treating a dental disease, wherein one or a plurality of compounds according to the invention, a mixture according to the invention, a curable blend according to the invention or a dental product according to the invention, preferably in one of the configurations identified as preferred, is/are used as a dental bonding agent, a dental filling material, a dental underfilling material, a flowable composite, a fissure sealer, as a root canal filling and sealing material, as a temporary restoration material (preferably temporary inlays, onlays, crowns, bridges, fixing materials) and/or as a stump build-up material.

EXAMPLES

The invention is further explained using the following examples. Unless otherwise indicated all data relate to the weight. The following abbreviations are used here:
BHT=2,6-di-tert.butyl-4-methyl phenol
UDMA=urethane dimethacrylate (7,7,9-trimethyl-4,13-dioxo-5,12-diazahexadecane-1,16-dioxydimethacrylate)
4-META=4-methacryloxy-ethyl trimellitate anhydride
CQ=campherquinone
DABE=ethyl-p-N,N-dimethylaminobenzoate
Bis-GMA=bisphenol-A-glycidyl-methacrylate
TEDMA=triethylene glycol dimethacrylate
TCD monomer=bis(methacrylolyoxymethyl)tricyclo[5.2.1.0$^{2,6}$]decane For the catalyst solution used in the following 0.50 g of dibutyltin(II)dilaurate were dissolved in 9.50 g of toluene.

Example 1

Synthesis of the Compound of Formula (1) (not According to the Invention)

3.80 g (19.36 mmol) of 3(4), 8(9)-bis(hydroxymethyl)tricyclo[5.2.1.0$^{2,6}$]decane were dissolved in 15 ml of tetrahydrofuran and 0.04 g of BHT and 0.105 g (approximately 0.1 mol. %) of the catalyst solution were added. Under agitation 3.00 g (19.34 mmol) of 2-isocyanatoethyl methacrylate dissolved in 10 ml of THF were dropped in. Once addition was complete the dropping funnel was replaced by a reflux condenser and the reaction mixture heated to 60° C. with the continuation of the reaction being monitored by IR spectroscopy. After 24 hours no further isocyanate bands could be detected. The solvent was removed using the rotary evaporator. The urethane of formula (1) was obtained in a yield of 6.66 g (18.95 mmol, corresponding to 98% of the theory).

Example 2

Synthesis of the Compound of Formula (3)

2.56 g (16.69 mmol) of POCl$_3$ were dissolved in 20 ml of methyl-tert-butyl ether and cooled to −78° C. Under vigorous agitation a mixture of 5.10 g (14.51 mmol) of the compound of Formula (1) from Example 1 and 1.69 g (16.69 mmol) of triethyl amine in 10 ml of methyl-tert-butylether were dropped in. Following this addition agitation was continued for an hour and the reaction mixture then had 0.91 g (50.79 mmol) of water and 3.67 g (36.28 mmol) of triethyl amine added at 0° C. Following agitation for a further hour at ambient temperature, the reaction mixture was recycled with 1% hydrochloric acid and then with water. The organic phase was dried over magnesium sulfate and the solvent then removed in the rotary evaporator. 3.85 g (8.90 mmol, corresponding to 61% of the theory) of compound (3) remained.

Example 3

Synthesis of the Compound of Formula (7) (not According to the Invention)

3.80 g (19.36 mmol) of 3(4), 8(9)-bis(hydroxymethyl)tricyclo[5.2.1.0$^{2,6}$]decane and 1.70 ml (1.66 g, 21.0 mmol) pyridine were dissolved in 50 ml of chloroform and then under ice cooling 1.89 ml (2.02 g, 19.36 mmol) methacrylic acid chloride, dissolved in 10 ml of chloroform, were dropped in. Once addition was complete agitation took place overnight at ambient temperature. The next day, 150 ml of 1N hydrochloric acid were added to the reaction mixture which was then transferred to a separating funnel and the phases separated. Then shaking out with saturated NaHCO$_3$— and NaCl solution took place followed by washing with water. The organic phase was dried over MgSO4 and the solvent removed following addition of 0.04 g BHT on the rotary evaporator. The methacrylic acid ester of formula (7) was obtained in a yield of 4.93 g (18.78 mmol, 97% of theoretical).

Example 4

Synthesis of the Compound of Formula (8) (not According to the Invention, See JP 2007091642A)

2.56 g (16.69 mmol) of POCl$_3$ were dissolved in 20 ml of methyl-tert-butyl ether and cooled to −78° C. Under vigorous agitation a mixture of 3.81 g (14.51 mmol) of the compound of Formula (7) from Example 3 and 1.69 g (16.69 mmol) of triethyl amine in 10 ml of methyl-tert-butylether were droppered in. Following this addition agitation was continued for an hour and the reaction mixture then had 0.91 g (50.79 mmol) of water and 3.67 g (36.28 mmol) of triethyl amine added at 0° C. Following agitation for a further hour at ambient temperature, the reaction mixture was recycled with 1% hydrochloric acid and then with water. The organic phase was dried over magnesium sulfate and the solvent then removed in the rotary evaporator. 3.85 g (10.45 mmol, or 72% of theoretical) of compound (8) remained.

Example 5

Synthesis of the Compound of Formula (21) (not According to the Invention)

The adhesive monomer (21) was prepared according to the synthesis sequence described in US 2006/0246017A1 under Example 2, swapping the 1,10-decanediole used there for 3(4), 8(9)-bis(hydroxymethyl)tricyclo[5.2.1.0$^{2,6}$]decane.

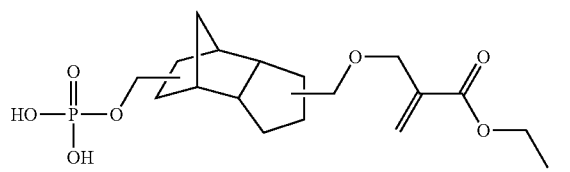

Formula (21)

Dental Compositions

The following compositions were prepared. Here the compositions A, B and F are comparative examples, while compositions C, D and E are blends according to the invention.

4-META is an adhesion promoting additive that is known for its very good bond-promoting characteristics and is used in many areas. Because of its successful and widespread use in dentistry it was used as reference.

The compositions of Examples A-H (in each case in parts by weight) and the results of the coefficient of adhesion measurements are listed in the following Tables. These compositions were prepared according to the non-etch method and without primer.

| | A | B | C | D | E | F | G | H |
|---|---|---|---|---|---|---|---|---|
| HEMA | 15.30 | 15.30 | 15.30 | 15.30 | 5.99 | 5.99 | 15.30 | 15.30 |
| UDMA | 7.65 | 7.65 | 7.65 | 7.65 | 2.99 | 2.99 | 7.65 | 7.65 |
| Bis-GMA | 7.65 | 0.00 | 7.65 | 0.00 | 2.99 | 2.99 | 7.65 | 7.65 |
| TCD monomer | 0.00 | 7.65 | 0.00 | 7.65 | 0.00 | 0.00 | 0.00 | 0.00 |
| 4-META | 30.61 | 30.61 | 0.00 | 0.00 | 0.00 | 12.02 | 0.00 | 0.00 |
| Adhesive monomer of Formula (3) | 0.00 | 0.00 | 30.61 | 30.61 | 12.02 | 0.00 | 0.00 | 0.00 |
| Adhesive monomer of Formula (8) (not according to the invention) | 0.00 | 0.00 | 0.00 | 0.00 | 0.00 | 0.00 | 30.61 | 0.00 |
| Adhesive monomer of Formula (21) (not according to the invention) | 0.00 | 0.00 | 0.00 | 0.00 | 0.00 | 0.00 | 0.00 | 30.61 |
| DABE | 0.28 | 0.28 | 0.28 | 0.28 | 0.11 | 0.11 | 0.28 | 0.28 |
| BHT | 0.06 | 0.06 | 0.06 | 0.06 | 0.02 | 0.02 | 0.06 | 0.06 |
| CC | 0.18 | 0.18 | 0.18 | 0.18 | 0.07 | 0.07 | 0.18 | 0.18 |
| Water | 7.65 | 7.65 | 7.65 | 7.65 | 2.99 | 2.99 | 7.65 | 7.65 |
| Acetone | 30.61 | 30.61 | 30.61 | 30.61 | 11.97 | 11.97 | 30.61 | 30.61 |
| Glass ceramic ($d_{50} = 1.5$ μm) | 0.00 | 0.00 | 0.00 | 0.00 | 39.91 | 39.91 | 0.00 | 0.00 |
| Glass ceramic ($d_{50} = 0.7$ μm) | 0.00 | 0.00 | 0.00 | 0.00 | 18.75 | 18.75 | 0.00 | 0.00 |
| Pyrogenic silicic acid | 0.00 | 0.00 | 0.00 | 0.00 | 2.16 | 2.16 | 0.00 | 0.00 |

Coefficients of Adhesion to Dentin

The following coefficients of adhesion to dentin were determined.

The coefficients of adhesion given are the average values from at least 5 individual measurements.

| | A | B | C | D | E | F | G | H |
|---|---|---|---|---|---|---|---|---|
| Coefficients of adhesion in MPa: | 9 | 10 | 15 | 19 | 15 | 4 | 11 | 8 |

Surprisingly the coefficients of adhesion of the composition C according to the invention are better than the coefficients of adhesion of the compositions G and H, in which monomer were used which were oriented towards the monomers from the prior art.

Measurement Method for Determination of the Coefficients of Adhesion

In order to determine the bonding characteristics of the dental compositions A through H the coefficients of adhesion were determined in extracted bovine teeth. The dentin test specimens were removed from an isotonic saline solution immediately before use, rinsed with water and treated with the composition under investigation straight away. The coefficients of adhesion are the average values from at least 5 measurements.

For Examples A Through D, G and H:

In order to simulate a fresh preparation, the exposed dentin surfaces were wet-ground using fine abrasive paper (1000 grade). The resultant surface should be flat and not dry out. Immediately prior to application excess moisture was blown away and the respective composition under examination was applied three times using a sponge or brush and massaged in for 10 seconds.

The respective composition was then photocured for 10 seconds with a blue light source (Celalux 2, VOCO GmbH Cuxhaven). Then a silicon ring with an internal diameter of 5 mm was placed on the cured surface without wiping away the existing inhibition layer of the respective composition.

In the opening of the silicon ring a photocurable filling composite with a methacrylate base (Grandio A1, batch 1019293, VOCO GmbH Cuxhaven) was then applied and photocured for 40 seconds (cylindrical test specimen (3 mm (high)×5 mm (diameter)). The finished specimens were stored in the testing cabinet at 37° C. and 100% relative humidity and after 24 hours the shear bond strength was determined using a universal testing machine (1 mm/min). Following measurement the exact dimensions of the test specimens were determined for calculation of the adhesion (expressed in MPa).

For Examples E and F (Bonding Cements)

For the investigations on the compositions E and F (bonding cements) the test specimen was prepared as described above. The respective cement was then applied on the ground surface in a sealed layer and worked into the hard dental material for 20 seconds. Then the respective cement was evenly distributed with the air syringe and photocured for 10 seconds (Celalux 2, VOCO GmbH Cuxhaven). Here it must be ensured that no pooling occurs and that the surface of the test specimen is evenly wetted. After curing a silicon ring with an internal diameter of 5 mm was positioned without damaging the inhibition layer within the ring and a filling composite (Grandio A1, batch 1019293, VOCO GmbH Cuxhaven) was introduced. After 40 seconds of photocuring the specimen was stored at 37° C. in the steam bath for 24 hours and then the shear bond strength was determined as described above.

Examples C through E were carried out by exchanging the adhesive monomer used there in each case of Formula (3) for corresponding compounds according to the invention with a bicyclo[2.2.1]heptane or tricyclo[3.3.1.1$^{3,7}$]decane structure. The parameter values determined are similar to those from Examples C through E.

The invention claimed is:

1. A compound of structure $(HO)_w-P(=O)-[G-(L)_x-Q(YZ)_b]_y$, wherein here and below the following applies:
each Q, independently of any other groups Q, represents a saturated or olefinically unsaturated polyalicyclic structure element selected from the group consisting of bicyclic, tricyclic, tetracyclic, pentacyclic and hexacyclic hydrocarbon radicals, wherein Q carries no further substituents or one or a plurality of substituents selected from the group consisting of alkyl groups, alkoxy groups, halogen atoms and trifluormethyl groups, index b is an integer selected from the group of integers 1, 2 and 3, each Z represents a structure element, which independently of any further structure elements Z is selected from the group consisting of

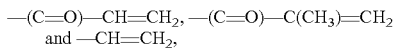
and —CH=CH$_2$, each Y represents a structure element, which—independently of any other structure elements Y—contains one or a plurality of N-atoms and the polyalicyclic structure element Q binds with Z in such a way that the chain of atoms binding Q with Z contains one or a plurality of N atoms, each structure element G, independently of any further structure elements G, represents either O or NH, each L represents a structure element which, independently of any further structure elements L, binds the group G with the polyalicyclic structure element Q, the index w is selected from the group of integers 0, 1 and 2, each index x independently of any further indices x represents either 0 or 1, the index y is selected from the group of integers 1, 2 and 3, wherein the total of w+y=3.

2. The compound as claimed in claim 1, wherein the compound has the following structure

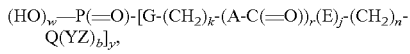

wherein the following applies:

each index k is an integer that, independently of any further indices k, is selected from the group of integers 0 through 12, each structure element A, independently of any further structure elements A, represents either O or NH, each structure element E, independently of any further structure elements E, represents either O or NH, each index r independently of any further indices r represents either 0 or 1, each index j independently of any further indices j represents either 0 or 1, each index n independently of any further indices n represents either 0 or 1, wherein if k=0, the index j represents 0 and the index r represents 0.

3. The compound as claimed in claim 1, comprising one, two or a plurality of functional groups selected from the group consisting of esters, urethane, N-acyl urethane, urea, N-acyl urea and amide, wherein the amide function is not directly linked with an N-atom, an O-atom or a carbonyl group.

4. The compound as claimed in claim 1, characterized in that the grouping YZ comprises a functional group selected from the group consisting of esters, urethane, N-acyl urethane, urea, N-acyl urea and amide, wherein the amide function is not directly linked with an N-atom, an O-atom or a carbonyl group.

5. The compound as claimed in claim 1, characterized in that the grouping YZ comprises a functional group selected from the group consisting of esters, urethane, N-acyl urethane, urea, N-acyl urea and methacrylamide.

6. The compound as claimed in claim 1, characterized in that the grouping YZ contains a functional group selected from the group consisting of urethane, N-acyl urethane, urea, N-acyl urea and methacrylamide, where the or at least one of the N-atoms of this functional group is positioned in the chain of atoms binding Q with Z.

7. The compound as claimed in claim 1, characterized in that the grouping YZ has a structure selected from the group consisting of

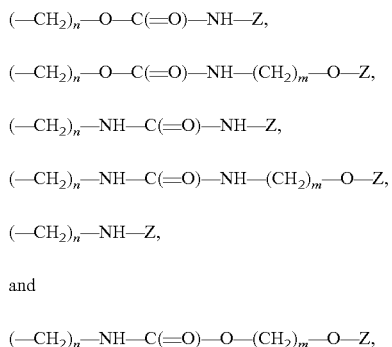

and

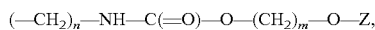

wherein Z and n have the meaning given above and wherein the following also applies:

each index m is an integer that, independently of any further indices m, is selected from the group of integers 1 through 12.

8. The compound as claimed in claim 1, wherein Q represents a polyalicyclic structure element, selected from the group consisting of bicyclic or tricyclic hydrocarbon radicals, wherein preferably none of the hydrogen atoms of this polyalicyclic structure element Q not already substituted by substituents YZ or by the respective group comprising the structure element G-(L)$_x$ is substituted.

9. The compound as claimed in claim 1, wherein the structure element Q represents a tricyclo[5.2.1.0$^{2,6}$]decane radical, a tricyclo[5.2.1.0$^{2,6}$]dec-3-ene radical, a tricyclo[3.3.1.1$^{3,7}$]decane radical or a bicyclo[2.2.1]heptane radical.

10. A method for preparing a compound of the structure (HO)$_w$—P(=O)-[G-(L)$_x$-Q(YZ)$_b$]$_y$ as claimed in claim 1, or a mixture comprising at least one compound of structure (HO)$_w$—P(=O)-[G-(L)$_x$-Q(YZ)$_b$]$_y$ as claimed in claim 1, comprising:

(i) providing a compound HG-(L)$_x$-Q(YZ)$_b$, (ii) reaction of the compound from step (i) with POCl$_3$ or phosphorous(V) oxide, preferably in the presence of an amine, (iii) hydrolysis of the reaction product formed in step (ii), wherein G, L, Q, Y, Z, w, x, b and y in each case have the above meanings, and wherein the molar quantity of the compound from step (i) per atom equivalent of phosphorous is in the range 0.5 through 6.

11. A mixture comprising one or two or a plurality of different compounds as claimed in claim 1.

12. A curable blend comprising (a) one or a plurality of compounds as claimed in claim 1, and (b) one or a plurality of further constituents selected from the group consisting of (b-1) monomers differing from constituent (a), which are copolymerizable with constituent (a), (b-2) one or a plurality of fillers, (b-3) monomers differing from constituent (a), which are copolymerizable with constituent (a), (b-4) photoinitiators and initiators for the chemical curing,
(b-5) solvents, and
(b-6) adhesion-promoting additives different from constituent (a).

13. The blend as claimed in claim 12, wherein the blend is a chemically and/or light-induced or heat-induced curing dental composition.

14. The blend as claimed in claim 12, wherein constituent (b-1) consists of or comprises
(b-1a) one or a plurality of (meth)acrylate monomers, selected from the group consisting of 2-hydroxyethyl methacrylate (HEMA), bisphenol-A-glycidyl-methacrylate (Bis-GMA), 7,7,9-trimethyl-4,13-dioxo-5,12-diazahexadecane-1,16-dioxy dimethacrylate (UDMA), triethylene glycol dimethacrylate (TEDMA), tetraethylene glycol dimethacrylate, polyethylene glycol dimethacrylate, trimethylolpropane trimethacrylate (TMPTMA), dodecanediol dimethacrylate (DODMA), glycerin di(meth)acrylate, 1,6-hexane diol dimethacrylate (HEDMA), ethoxylated bisphenol-A-dimethacrylate, pentaerythritol dimethacrylate, pentaerythritol-tri(meth)acrylate and dipentaerythritolpenta(meth)acrylate,
and/or
(b-1b) one or a plurality of monomers selected from the group consisting of compounds of structure $Q^a(MX_e)_h$, where the following applies:
$Q^a$ is a polyalicyclic structure element and has, independently of the meaning of the structure element Q in compounds of constituent (a), the meaning given above for Q,
h is an integer selected from the group of integers 1, 2, 3 and 4,
each X represents a structure element, which independently of any further structure elements X is selected from the group consisting of

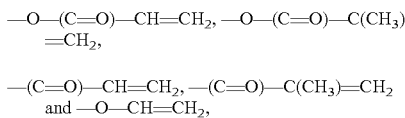

each index e is an integer, which independently of any further indices e is selected from the group of integers 1, 2, 3 and 4,
each M represents a structure element which, independently of any further structure elements M, in the structure $Q^a(MX_e)_h$ binds the polyalicyclic structure element $Q^a$ with e structure elements X.

15. The blend as claimed in claim 12, characterized in that component
(b-1b) comprises or consists of
bis(methacryloyloxymethyl)tricyclo[5.2.1.0$^{2,6}$]decane and/or
bis(acryloyloxymethyl)tricyclo[5.2.1.0$^{2,6}$]decane.

16. A product obtained by curing a compound as claimed in claim 1.

17. A dental material comprising the compound of claim 1.

18. A method of preparation of a dental material comprising: applying a compound as claimed in claim 1.

19. The method according to claim 18, wherein said method comprises:
preparing bonding agents, preferably dental bonding agents,
preparing filling and/or sealing materials, preferably dental filling materials, underfilling materials, fissure sealing materials, root canal filling and/or sealing materials,
preparing lacquers, preferably gloss lacquers and/or surface lacquers, preferably dental gloss lacquers and/or surface lacquers,
preparing flowable composite materials (flow materials), preferably dental composite materials,
preparing dental temporary restoration materials and/or stump build-up materials, or
preparing adhesive, coloring, painting or coating compositions, compounds, sealants, fillers, laminating resins, molding masses, binding agents or casting resins.

20. The method according to claim 18, wherein said method is part of a dental procedure for treating a dental disease.

21. A method for preparing a product, comprising: (i) providing a compound as claimed in claim 1.